(12) United States Patent
Miura et al.

(10) Patent No.: US 6,361,919 B1
(45) Date of Patent: Mar. 26, 2002

(54) SILVER HALIDE PHOTOGRAPHIC LIGHT SENSITIVE MATERIAL AND HYDRAZINE COMPOUND EMPLOYED IN IT

(75) Inventors: Norio Miura; Mitsunori Matsuura; Kiyoshi Fukusaka, all of Hino (JP)

(73) Assignee: Konica Corporation (JP)

( * ) Notice: Subject to any disclaimer, the term of this patent is extended or adjusted under 35 U.S.C. 154(b) by 0 days.

(21) Appl. No.: 09/460,750

(22) Filed: Dec. 14, 1999

(30) Foreign Application Priority Data

Dec. 16, 1998 (JP) .......................................... 10-357465

(51) Int. Cl.$^7$ ................................................. G03C 1/10
(52) U.S. Cl. ........................................................ 430/264
(58) Field of Search ......................................... 430/264

(56) References Cited

U.S. PATENT DOCUMENTS

| | | | |
|---|---|---|---|
| 5,480,886 A | 1/1996 | Yamazaki et al. | 430/264 |
| 6,017,674 A * | 1/2000 | Ezoe et al. | 430/264 |

FOREIGN PATENT DOCUMENTS

| | | |
|---|---|---|
| DE | 3536107 | 6/1986 |
| EP | 0496342 | 7/1992 |
| EP | 0639559 | 2/1995 |
| EP | 0740196 | 10/1996 |
| EP | 0807850 | 11/1997 |
| FR | 7413166 | 4/1974 |
| JP | 8231528 | 10/1996 |
| WO | 9319040 | 9/1993 |

OTHER PUBLICATIONS

European Search Report EP 99 31 0050.
XP–002129548, p. 445, 22 Physical Org. Chem. vol. 90, 1979.
XP–002129549, p. 751, 28–Heterocyles, vol. 88, 1978.
XP–002129547, pp. 4399 to4428, Catalytic Asymmetric Amination of Ketones via Highly Enantioselective Hydrogenation of the C=N Double Bond, vol. 50, No. 15.
XP–002129544, Chem. Ber. 116, 1787–1821 (1983), C. Ruchard, et al.
XP–002129545, Diazenes. VI. Alkyldiazenes[1], pp. 1992 to 1999.
XP–002129546, J. Org. Chem. 1981, 46, 2082–2089.

* cited by examiner

*Primary Examiner*—Hoa Van Le
(74) *Attorney, Agent, or Firm*—Bierman, Muserlian and Lucas

(57) ABSTRACT

A silver halide photographic photosensitive material is disclosed. The silver halide photographic photosensitive material comprises a hydrazine compound at least one alkyl group which has no atom other than carbon and hydrogen atoms, has three or more branches, and does not bond to aromatic ring directly.

20 Claims, No Drawings

SILVER HALIDE PHOTOGRAPHIC LIGHT SENSITIVE MATERIAL AND HYDRAZINE COMPOUND EMPLOYED IN IT

FIELD OF THE INVENTION

The present invention relates to a novel hydrazine compound, silver halide photographic photosensitive material containing it and an image forming method, in particular a novel hydrazine compound, silver halide photographic photosensitive material containing it for graphic arts and an image forming.

BACKGROUND OF THE INVENTION

The graphic includes process of production to convert original image of continuous gradation into dot image. The technology such as to reproduce an ultra contrast image ($\gamma$ of 10 or more) is expected in this process, and film for graphic arts employing infectious development of hydrazine compound broadly practiced. In late years high performance such as high sensitivity, low pH developing suitability, reductone developing suitability in response to output films employed in an image setter having oscillating wavelengths of 600 to 800. Developer composition having pH of 10.4 or developer composition employing reductone developing agent such as ascorbic acid and erythorbic acid becomes spreading from the viewpoint of environment suitability broadly, but, the conventional silver halide photographic photosensitive material using hydrazine compound has disadvantage such that the sensitivity and gamma extremely fall down and fog of pepper spots occurs employed in combination with these developer compositions.

SUMMARY OF THE INVENTION

An object of the present invention to provide a hydrazine compound having high activity, and, by employing it, a silver halide photographic photosensitive material by which enough sensitivity and contrast and difficult to occur fog of pepper spots are obtained when the developer composition of lower pH or the developer composition containing the reductone as a developing agent are used, and image forming method thereof.

The above object of the present invention is achieved by the following method.

1. A hydrazine compound which is characterized by comprising at least one alkyl group which has no atom other than carbon and hydrogen atoms, has three or more branches, and does not bond to aromatic ring directly.

2. The hydrazine compound described in above mentioned item 1 wherein total number of carbon atoms of the alkyl group is 6 to 10.

3. The hydrazine compound described in above mentioned item 1 wherein the alkyl group is 2,4,4-trimethylpentyl group.

4. The hydrazine compound represented by the following formula (1).

Formula (1)

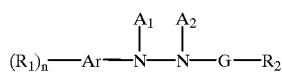

In the formula $R_1$ is a group containing at least one alkyl group which has no atom other than carbon, has three or more branches, and does not bond to aromatic ring directly; n is an integer of 0 to 3; Ar is an aromatic group, $A_1$ and $A_2$ are both are hydrogen atom or one of them is a hydrogen atom and the other is an alkylsulfonyl or acyl group; $R_2$ represents alkyl group, aryl group, heteroaryl group, alkenyl group, alkoxy group or amino group; and G is —(CO)p— group, sulfonyl group, sulfoxy group, —P(=O)$R_3$— group or iminomethylene group, p is an integer of 1 or 2, $R_3$ is alkyl group, alkenyl group, alkynyl group, aryl, alkoxy group, alkenyloxy group, alkynyloxy group, aryloxy group or amino group.

5. The hydrazine compound described in above mentioned item 4 wherein total number of carbon atoms of the alkyl group in the formula (1) is 6 to 10.

6. The hydrazine compound described in above mentioned item 4 wherein the alkyl group a formula (1) is 2,4,4-trimethylpentyl group.

7. The hydrazine compound described in above mentioned item 4 to 6 wherein $R_2$ of a formula (1) is trifluoromethyl group.

8. A hydrazine compound represented by the following formula (2).

Formula (2)

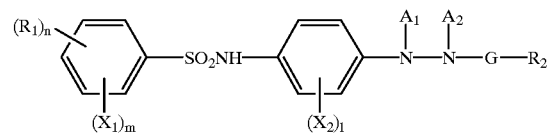

In the formula $R_1$, n, $A_1$, $A_2$, G and $R_2$ are the same meaning as $R_1$, n, $A_1$, $A_2$, G and $R_2$ in the formula (1) respectively. $X_1$ and $X_2$ represent a hydrogen atom or a group which can be substituted for benzene ring. m and l each represents an integer of 0 to 4, with proviso m+n<5.

9. The hydrazine compound described in above mentioned item 8 wherein total number of carbon atoms of the alkyl group which $R_1$ has in the formula (2) is 6 to 10.

10. The hydrazine compound described in above mentioned item 8 wherein the alkyl group which $R_1$ has in the formula (2) is 2,4,4-trimethylpentyl group.

11. The hydrazine compound described in above mentioned item 8 wherein the alkyl group which $R_1$ has in the formula (2) is trifluoromethyl group.

12. A silver halide photographic photosensitive material which comprises at least one kind of hydrazine compound describing in claims 1 to 11.

13. A silver halide photographic photosensitive material which comprises at least one kind of hydrazine compound describing in claims 1 to 11 and at least of hydrazine compound the following formula (3).

Formula 3

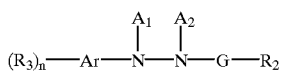

In the formula $R_3$ represents a group containing at least one two-valent sulfur atom. n is an integer of 0 to 3. Ar, $A_1$, $A_2$, G and $R_2$ are the same meaning as Ar, $A_1$, $A_2$, G and $R_2$ in the formula (1) respectively.

14. The silver halide photographic photosensitive material described in above mentioned item 13 wherein $R_3$ in the formula (3) is a group containing alkylthio group having 8 or less carbon atoms.

15. Silver halide photographic photosensitive material described in above mentioned item 13 or 14 wherein $R_3$ in the formula (3) is trifluoromethyl group.

16. Image forming method which forms an image by developing process at least one of the silver halide photographic photosensitive material described in claim 12 to 15 after exposing by using laser light source, and a picture is formed of silver halide photographic photosensitive material described in item 12 to 15.

17. An image forming method described in above mentioned item 16 wherein the developer composition employed in the developing process containing a developing agent represented by formula (A).

Formula A

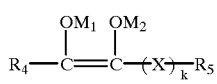

In the formula $R_4$ and $R_5$ each represents an alkyl group, amino group, alkoxy group or alkylthio group, $R_4$ and $R_5$ may form ring by bonding mutually; X represents a carbonyl group or thiocarbonyl group, k represents 0 or 1. $M_1$ and $M_2$ each represent a hydrogen atom or an alkali metal.

18. The image forming method described in abovementioned item 16 or 17 wherein pH of the developer composition employed in the developing processing is 7.5 to 10.

DETAILED DESCRIPTION OF THE INVENTION

The invention is described in detail below.

The hydrazine compound of the invention is described at first.

In counting number of the branches which the alkyl group has appeared in the term of "three or more branches" in the "alkyl group which has no atom other than carbon, has three or more branches, and does not bond to aromatic ring directly" in claims in the present invention, the alkyl group has a branch for a secondary carbon atom and two branches for a tertiary carbon atom, and the total numbers of branches are summed up.

In the present invention, the "alkyl group which has no atom other than carbon, has three or more branches, and does not bond to aromatic ring directly" are mentioned preferably, for example, as the following groups.

| | | Number of Branches |
|---|---|---|
| (R-1) | 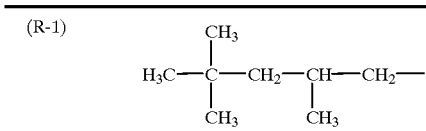 | 3 |
| (R-2) | 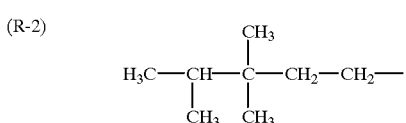 | 3 |

-continued

| | | Number of Branches |
|---|---|---|
| (R-3) | H₃C—CH—CH—CH—CH₂— <br>         │    │    │ <br>         CH₃ CH₃ CH₃    with CH₃ on middle CH | 3 |
| (R-4) | H₃C—CH—CH₂—C—CH₂— with CH₃ branches | 3 |
| (R-5) | H₃C—C(CH₃)₂—CH₂—CH(CH₃)— | 3 |
| (R-6) | H₃C—CH(CH₃)—CH(CH₃)—CH(CH₃)— | 3 |
| (R-7) | H₃C—C(CH₃)₂—CH(CH₃)—CH₂— | 3 |
| (R-8) | H₃C—C(CH₃)₂—CH(CH₃)— | 3 |
| (R-9) | H₃C—CH(CH₃)—C(CH₃)₂— | 3 |
| (R-10) | H₃C—C(CH₃)₂—CH₂—C(CH₃)₂— | 4 |
| (R-11) | H₃C—C(CH₃)₂—CH(CH₃)—C(CH₃)₂— | 5 |
| (R-12) | H₃C—C(CH₃)₂—CH₂—C(CH₃)₂—CH₂— | 4 |
| (R-13) | H₃C—C(CH₃)₂—CH₂—C(CH₃)₂—CH₂—C(CH₃)₂—CH₂— | 6 |

-continued

| | | Number of Branches |
|---|---|---|
| (R-14) | [structure: dimethylcyclohexyl group with H₃C, H₃C substituents] | 3 |
| (R-15) | H₃C—C(CH₃)(CH₃)—CH₂—C(CH₃)(CH₃)—CH₂—CH₂— | 4 |
| (R-16) | H₃C—CH₂—C(CH₂CH₃)(CH₂CH₃)—CH— with H₃C—CH₂ | 3 |
| (R-17) | H₃C—CH(CH₃)—CH₂—C(CH₃)(CH₃)— | 3 |
| (R-18) | [structure: trimethylcyclohexyl group with three H₃C substituents] | 4 |
| (R-19) | H₃C—C(CH₃)(CH₃)—CH₂—CH(CH₃)—CH₂—CH₂— | 3 |
| (R-20) | H₃C—C(CH₃)(CH₃)—CH₂—CH(CH₃)—CH(CH₂CH₃)—CH₂— | 4 |

Preferably, among the above groups, the number of carbon atom is 6 to 10, and in particular preferably, the number of carbon atom is 8, and most preferable is 2,4,4-trimethyl pentyl group represented by (R-1).

Next the hydrazine compound represented by a formula (1) is described.

In a formula mentioned above (1), the group represented by $R_1$ is preferably a group exemplified below, each of which comprises an alkyl group as a part of the group, and the alkyl group does not contain constructing atom except carbon and hydrogen and have three or more branches. The examples of the group include amino group, acyl group, alkoxycarbonyl group, aryloxy carbonyl group, acylamino-group, alkoxycarbonylamino group, aryloxy carbonylamino group, sulfonyl amino group, sulfamoyl group, carbamoyl group, alkylsulfonyl group, aryl sulfonyl group, sulfinyl group, ureide group, silyl group, heterocyclic group, alkylthio group, arylthio group etc. More preferable are acylamino group, carbamoyl group, ureide group, amino group, sulfonyl amino group, and alkylthio group, and in particular acylamino group is preferable. Examples of the alkyl group which has no atom other than carbon, has three or more branches, and does not bond to aromatic ring directly are preferably the groups of above mentioned (R-1) to (R-20). Among those the preferable group is that having carbon atoms of 6 to 10, more preferably carbon numbers of 8 and particularly preferably 2,4,4-trimethylpentyl group of (R-1).

The aromatic group represented by Ar includes heteroaromatic group, but preferably is non-heteroaromatic group. Especially preferably it is benzene ring group. It is preferable that both $A_1$ and $A_2$ are hydrogen atoms. As for $R_2$, it is preferable to be alkyl group, particularly substituted alkyl group with halogen atom, and trifluoroacetyl group is most preferable. As for G, oxalyl group and carbonyl group are preferable, and particularly carbonyl group is preferable.

Next the hydrazine compound represented by a formula (2) is described.

Preferable example of the group which is capable of substituting the benzene ring represented by $X_1$ and $X_2$ in a formula (2) mentioned above, includes alkyl group, alkenyl group, alkynyl group, aryl group, amino group, alkoxy group, aryloxy group, acyl group, alkoxycarbonyl group, aryloxycarbonyl group, acyloxy group, acylamino group, alkoxycarbonylamino group, aryloxy carbonylamino group, sulfonylamino group, sulfamoyl group, carbamoyl group, alkylthio group, arylthio group, sulfonyl group, sulfinyl group, ureide group, hydroxy group, mercapto group, halogen atom, hydrazino group, and heterocyclic group. The substituent may be substituted furthermore. In case there is two or more substituents, they may be same or different. Especially preferably is alkyl group, and most preferably is methyl group. It is preferable that m is an integer of 0 to 2, and most preferably is 2. As for 1, 0 is preferable.

Next the hydrazine compound represented by formula (3) is described.

As preferable examples of a group containing at least one of 2-equivalent sulfur atom represented by $R_3$ in the formula (3) mentioned above listed as mercapto group, alkylthio group, arylthio group, thioacyl group, alkoxy thiocarbonyl group, aryloxy thiocarbonyl group, thioacyl amino group, alkoxy thiocarbonyl amino group, aryloxy thiocarbonyl amino group, thiocarbamoyl group, thiouredide group, and heterocyclic thione group. Mercapto group, thiouredide group, alkylthio group, and arylthio group are preferable. Especially alkylthio group is preferable. Carbon number of alkyl group of the alkylthio group is preferably eight or less, and especially preferably is five or less. The most preferable carbon number is 5.

Concrete examples of the hydrazine compound represented by formulae (1) and (2) are described in the following.

H1-1
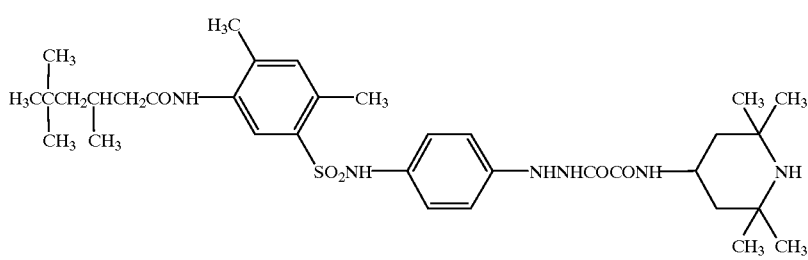
H1-2
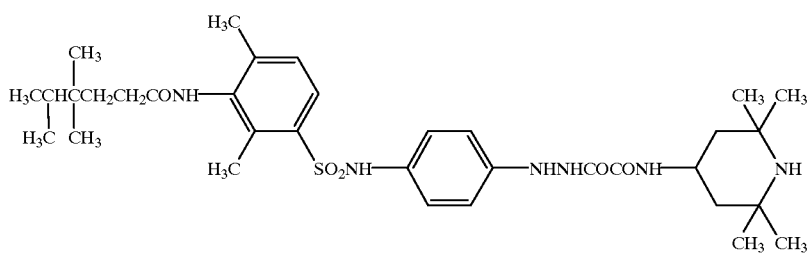
H1-3
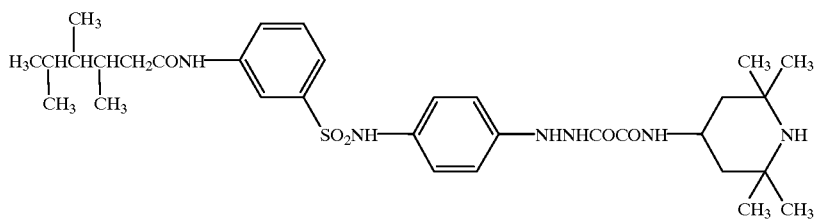
H1-4
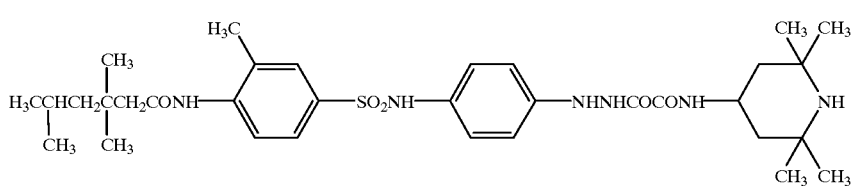
H1-5
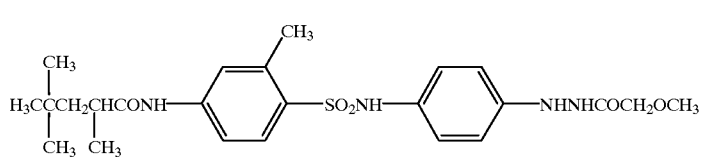
H1-6
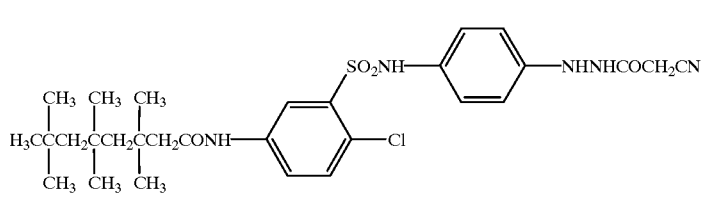
H1-7
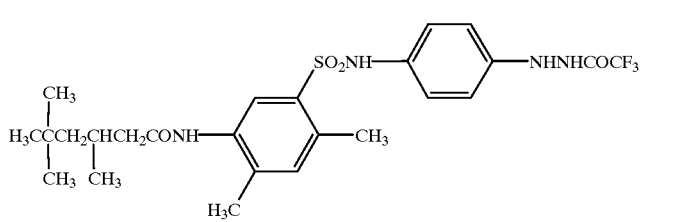

-continued
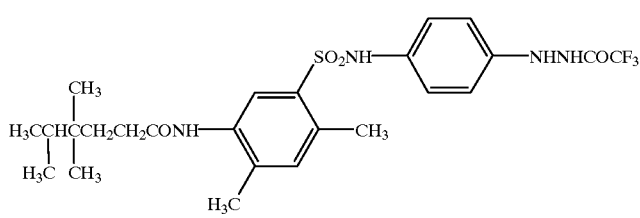
H1-8
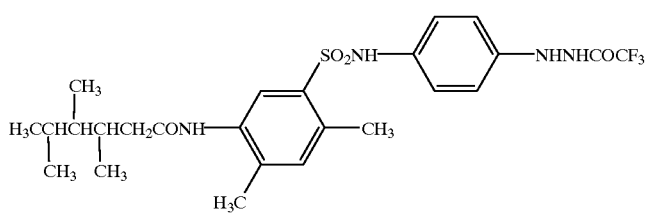
H1-9
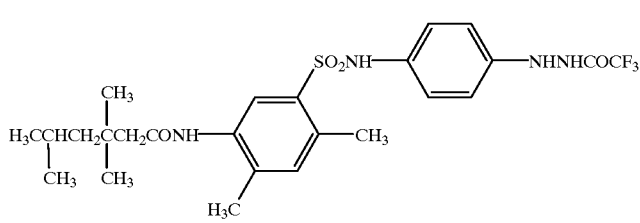
H1-10
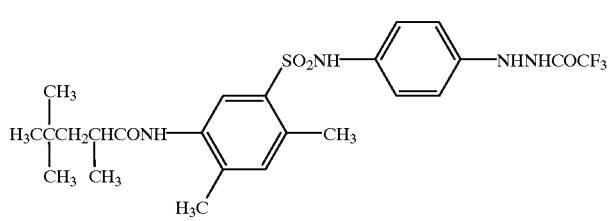
H1-11
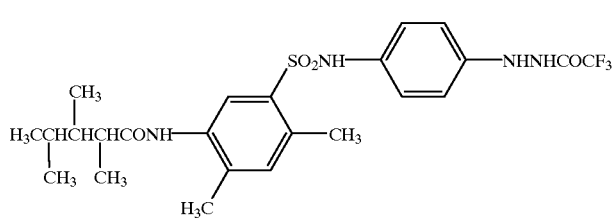
H1-12
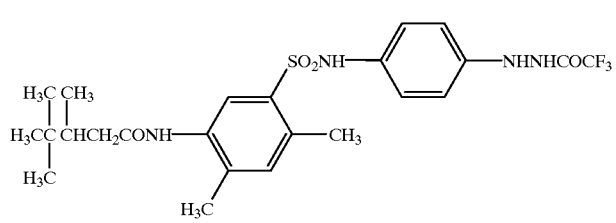
H1-13
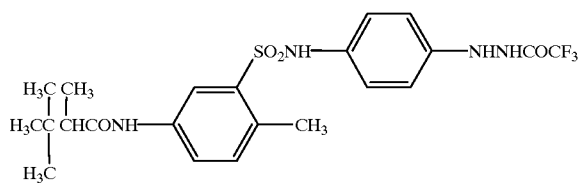
H1-14

-continued
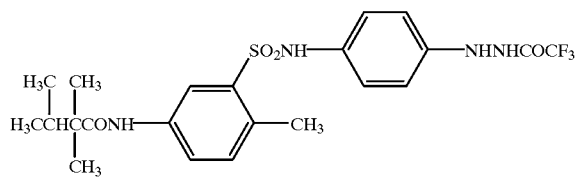
H1-15
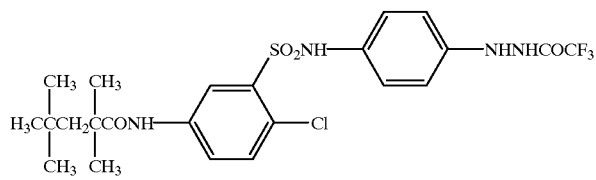
H1-16
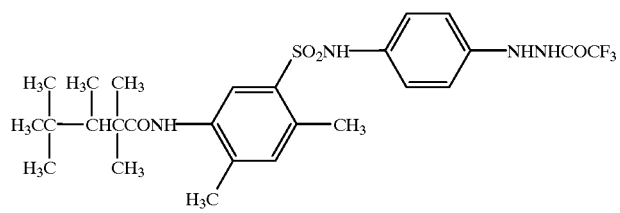
H1-17
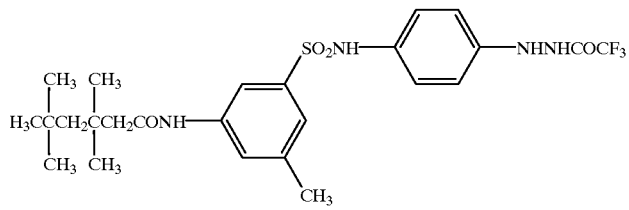
H1-18
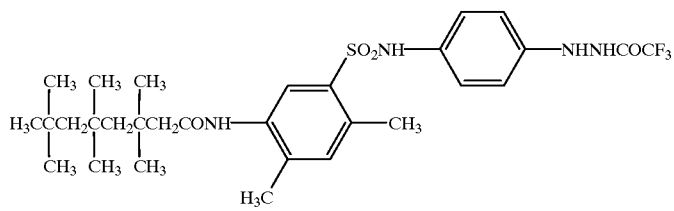
H1-19
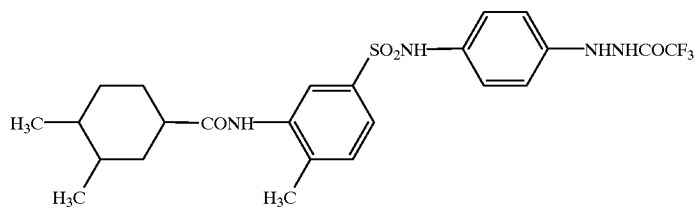
H1-20
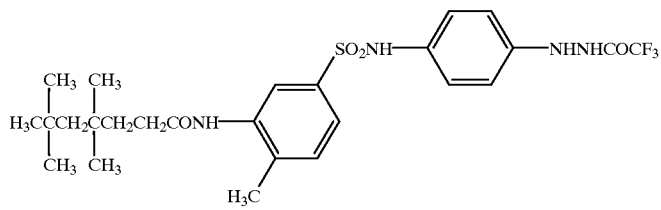
H1-21

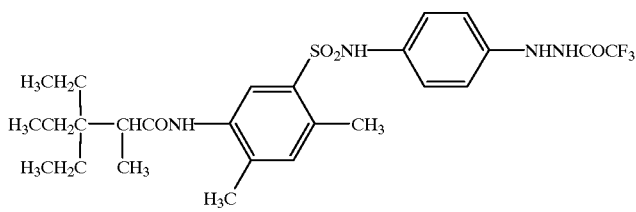
H1-22
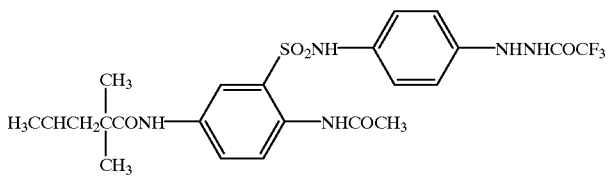
H1-23
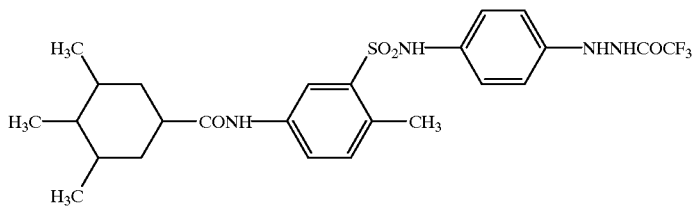
H1-24
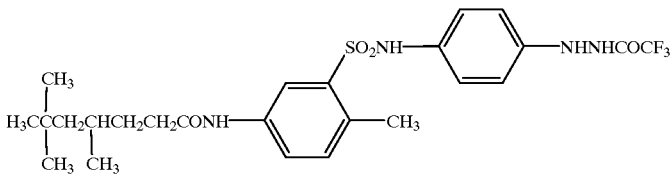
H1-25
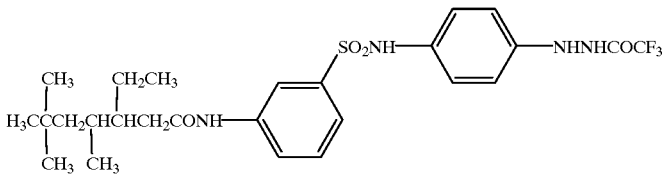
H1-26
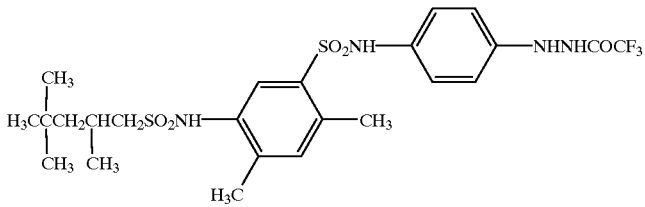
H1-27
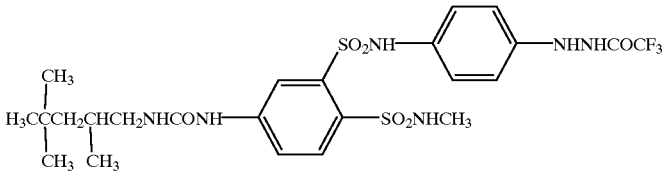
H1-28

H1-29
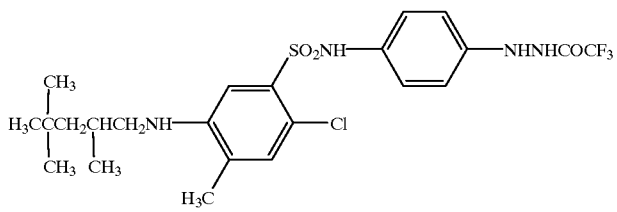
H1-30
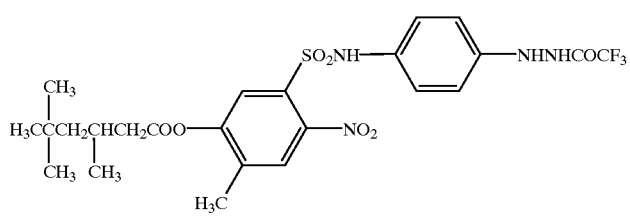
H1-31
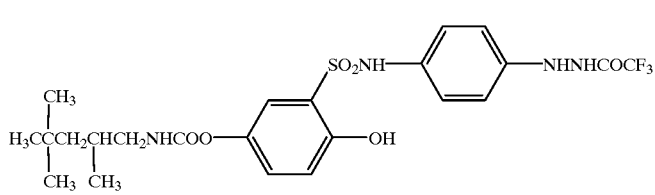
H1-32
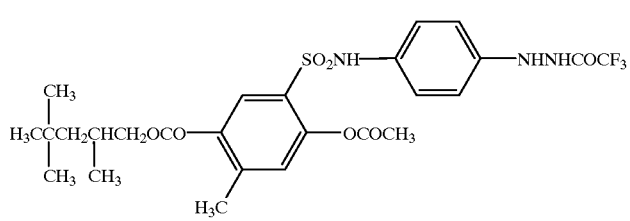
H1-33
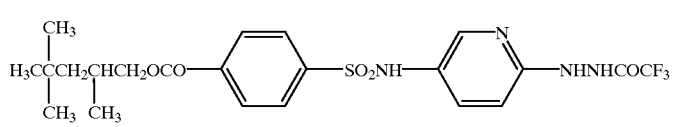
H1-34
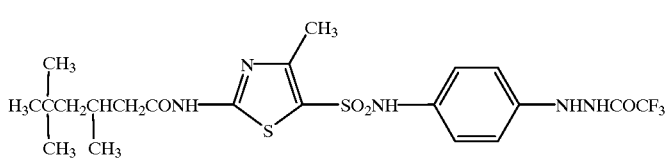
Concrete examples of the hydrazine compound represented by formula (3) are described in the following.
H2-1
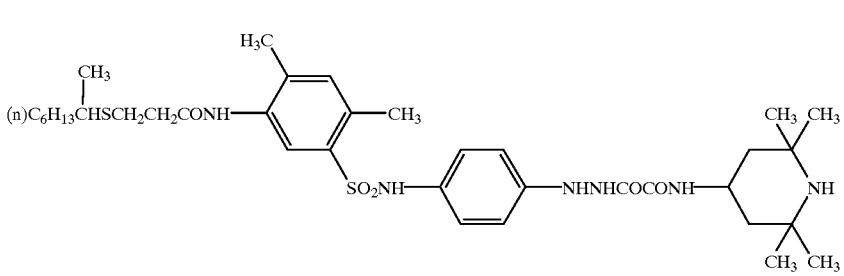

H2-2
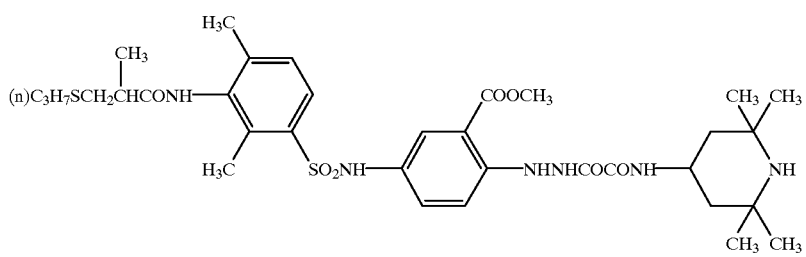
H2-3
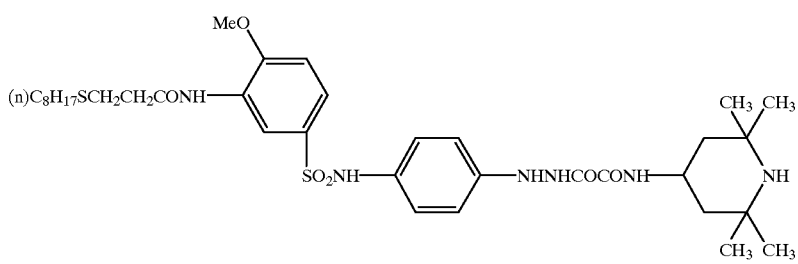
H2-4
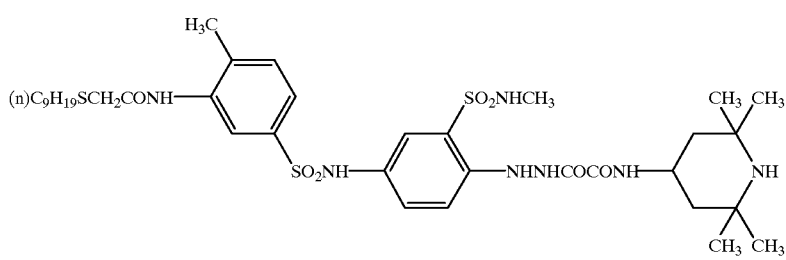
H2-5
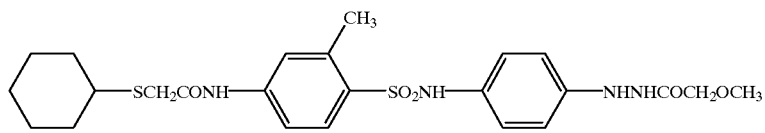
H2-6
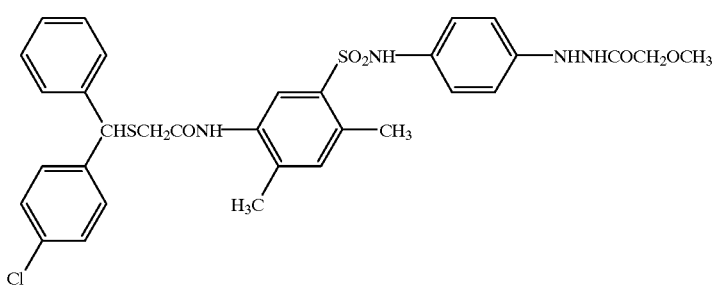
H2-7
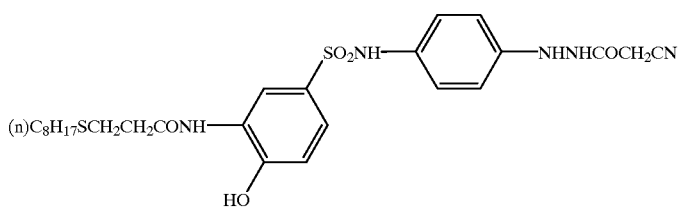
H2-8
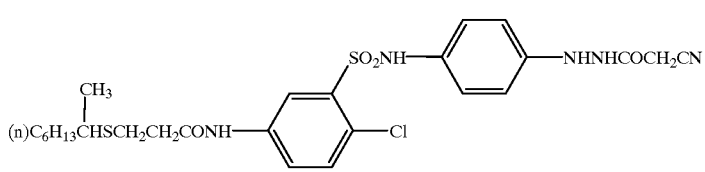

-continued
H2-9
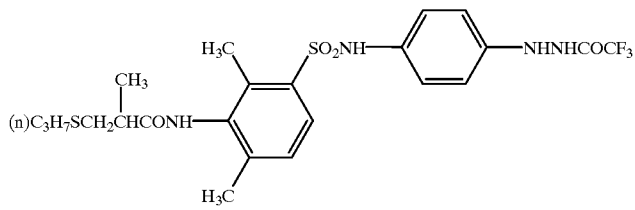
H2-10
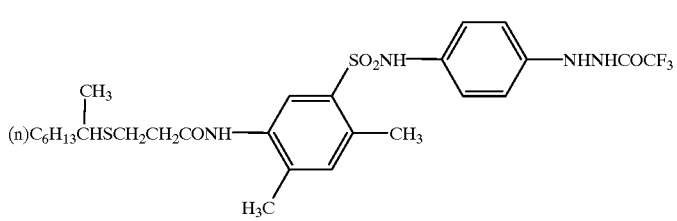
H2-11
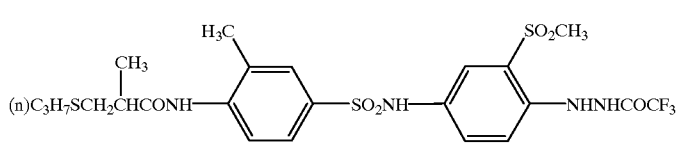
H2-12
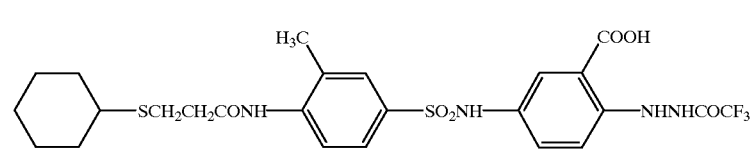
H2-13
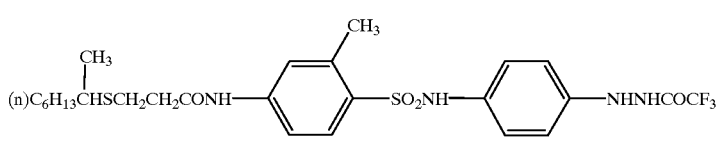
H2-14
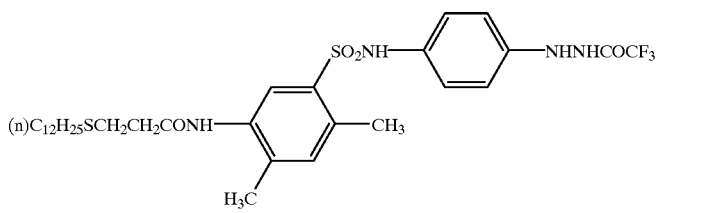
H2-15
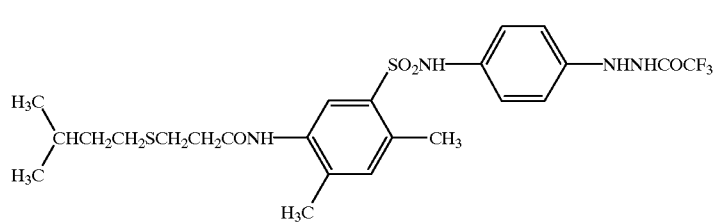
H2-16
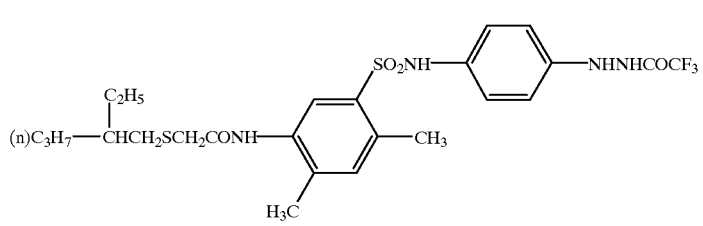

-continued
H2-17
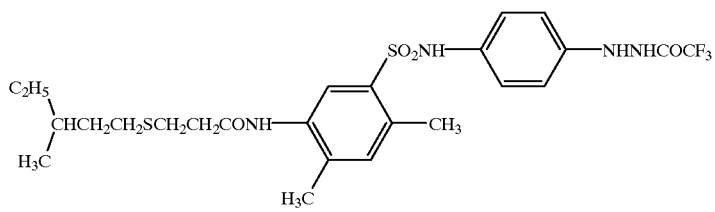
H2-18
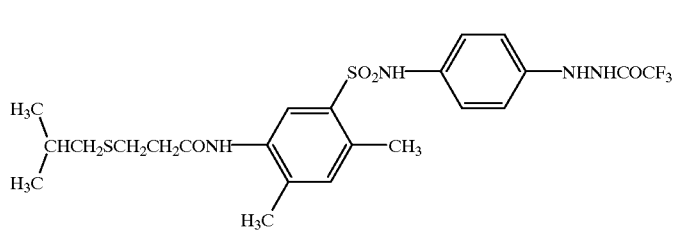
H2-19
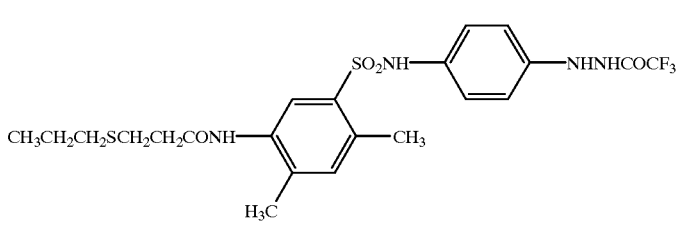
H2-20
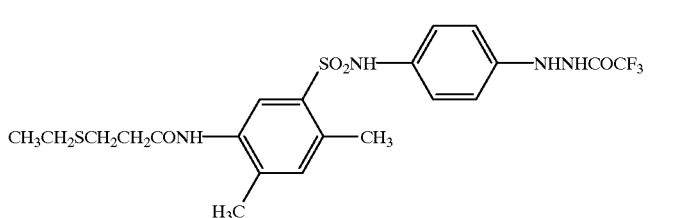
H2-21
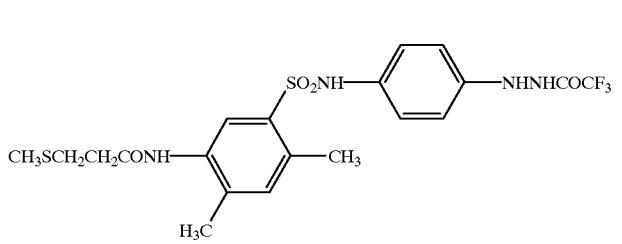
H2-22
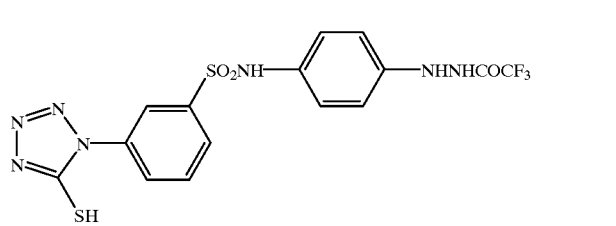
H2-23
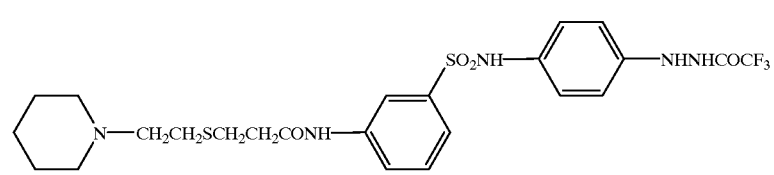

-continued
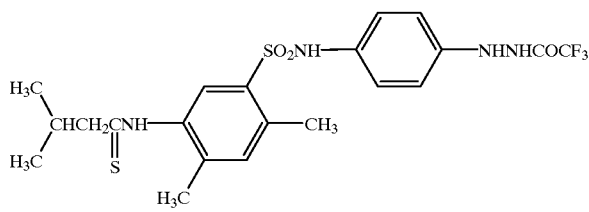
H2-24
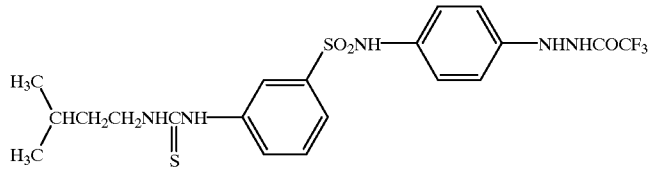
H2-25
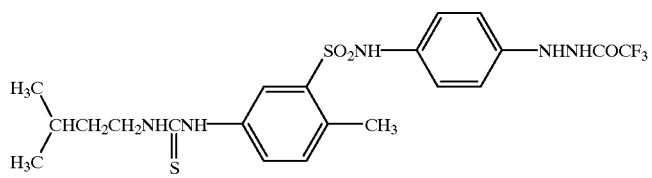
H2-26
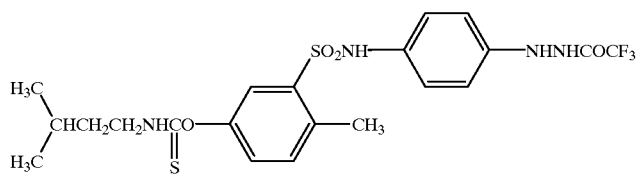
H2-27
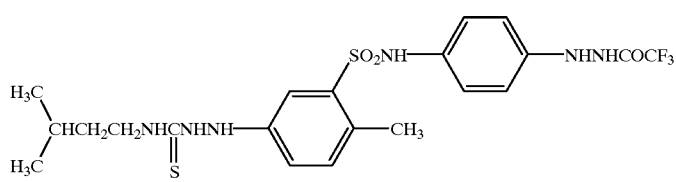
H2-28
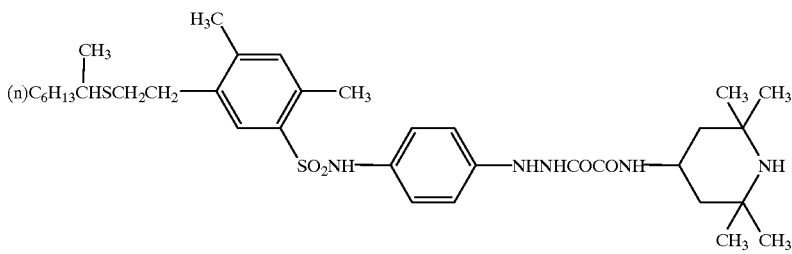
H2-29
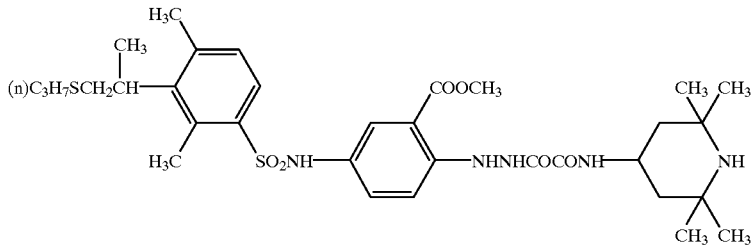
H2-30

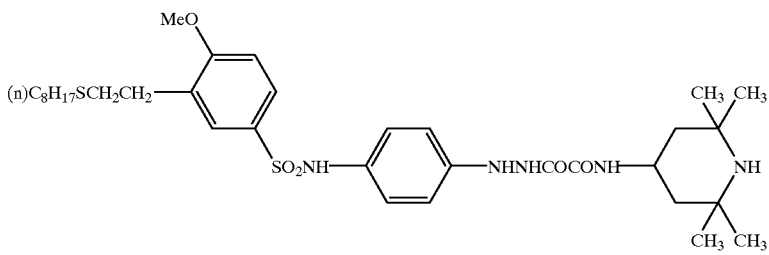

H2-31

Hydrazine compound employed by the present invention can be easily synthesized by conventionally known method.

An example of synthesis method is shown below. The other hydrazine compounds of the present invention can be synthesized in accordance with the example.

Synthesis Example 1

Synthesis of Compound Example H1-7

1. Synthesis of sulfonic acid (7S)

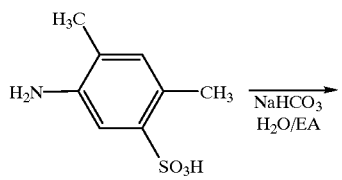

| Xylidine-5-sulfonic acid | 64.1 g (0.31 mol) |
| Acid chloride (7A) | 75.6 g (1.3 equivalent) |
| Sodium hydrogencarbonate | 80.4 g (3.0 equivalent) |
| Ethylacetate | 200 ml |
| Water | 500 ml |

(1) Dissolve sodium hydrogencarbonate in 500 ml of water, and add xylidine-5-sulfonic acid it, then stir.

(2) Add 200 ml of ethyl acetate, and drip acid chloride (7 A) at low temperature (7–10° C.) with ice bath.

(3) Stir for one hour by cooling with ice.

(4) Raise the temperature to room temperature and stir for 30 minutes.

(5) Add water, and adjust pH to 1 with concentrated hydrochloric acid.

(6) Extract with ethyl acetate.

(7) Wash the ethyl acetate layer with saturated aqueous salt solution.

(8) Dry the ethyl acetate layer with sodium sulfate, and remove solvent by evaporation under reduced pressure.

Obtained is 87.2 g brown solid. Yield 80.2%

2. Synthesis of sulfonyl chloride (7SC)

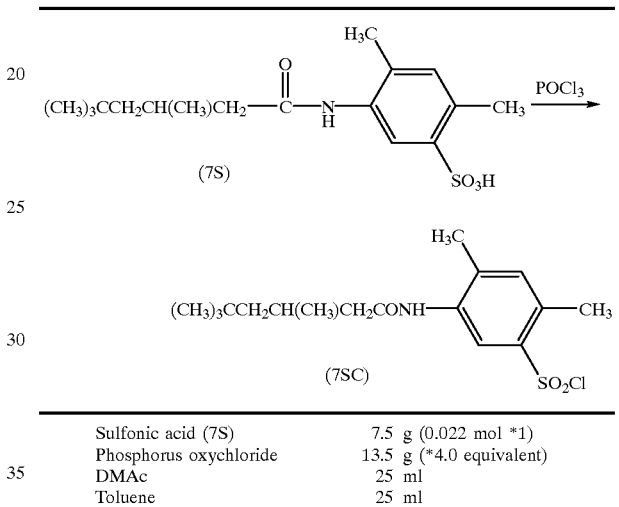

| Sulfonic acid (7S) | 7.5 g (0.022 mol *1) |
| Phosphorus oxychloride | 13.5 g (*4.0 equivalent) |
| DMAc | 25 ml |
| Toluene | 25 ml |

*1: calculated in such way as the purity obtained in prior process being 100%

(1) Dissolve sulfonic acid in 25 ml of dimethylacetamide (DMAc) and 25 ml of toluene solution, and lose phosphorus oxychloride with (5–10° C.) by cooling with ice.

(2) Stir for one hour by cooling with ice.

(3) Raise the temperature to room temperature and stir for one hour.

(4) Add toluene, and pour into 1L of crushed ice.

(5) Stir for 30 minutes, then take the toluene layer, and extract water layer with toluene.

(6) Dry the toluene layer with magnesium sulfate.

(7) Remove magnesium sulfate, and remove solvent by evaporation under reduced pressure.

Obtained is 8.1 g of brown liquid. Yield 102%. It is used for the next process without treatment.

3. Reduction of nitro compound (7N)

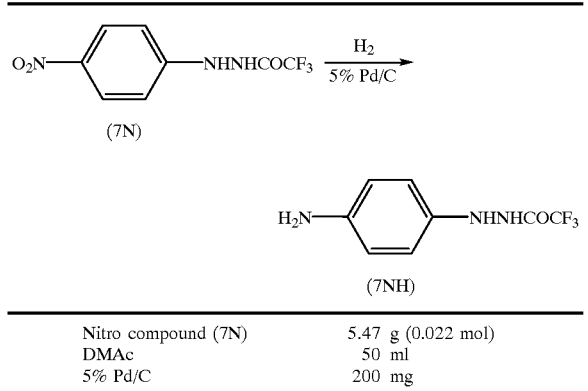

| Nitro compound (7N) | 5.47 g (0.022 mol) |
|---|---|
| DMAc | 50 ml |
| 5% Pd/C | 200 mg |

(1) Dissolve nitro compound (7N) in DMAc, and add 5% Pd/C, and subject to normal pressure catalytic reduction.

(2), Filter the reaction product with diatomaceous earth after completion of reaction. The resulted amino compound (7NH) is employed in the next reaction process.

4. Synthesis of H1-7

Sulfonyl chloride (7SC) 8.1 g (0.022 mol)
(Obtained by Process 2., mentioned above)
Amino compound (7NH) (0.022 mol)
(Above-mentioned DMAc solution is used)
Pyridine 1.91 g (1.1 equivalent)

(1) Add pyridine to the above-mentioned amino compound (7NH) solution, and drip sulfonyl chloride (7SC) by cooling with ice at 10–15° C.

(2) Stir for one hour by cooling with ice, then raise the temperature to room temperature, afterwards stir for 30 minutes.

(3) Pour into the water, and extract with ethyl acetate.

(4) Wash the ethyl acetate layer with saturated aqueous salt solution after rinsing with 1.2N hydrochloric acid.

(5) Dry the ethyl acetate layer with magnesium sulfate, and remove solvent by evaporation under reduced pressure.

(6) Dissolve the residue in 70 ml of ethanol, and drip the obtained in 700 ml of 2.5% salt aqueous solution.

(7) Take the deposit material by filtration, rinse it with water, press enough, and dry with air at 40° C. Exemplified compound H1-7 as the object, 8.0 g of lemon yellow solid compound is obtained (Yield 67%). Melting point is 197° C.

The structure is identified by NMR spectrum and MASS spectrum.

The hydrazine compound of the invention is added in the silver halide emulsion layer or a layer adjacent to it. The hydrazine compound of the invention is employed in any layer of silver halide emulsion layer side, and is preferably in silver halide emulsion layer or the adjacent layer to it. The optimum amount varies in accordance with grain size of silver halide, halogen composition, quantity of chemical sensitization, kind of inhibitor, and in the range of $10^{-6}$ to $10^{-1}$ mol is preferable per 1 mol silver halide in general, and in the range of $10^{-5}$ to $10^{-2}$ mol is particularly preferable. Preferably at least one kid of the hydrazine compound described in claims 1–11 and at least one kid of the hydrazine compound described in claims 13–15 are used in the silver halide photographic photosensitive material of the invention in combination as described in claim 13. Especially combination use of one kind of hydrazine compound of formula (2) and one kind of that of formula (3) is. Ratio of content of the hydrazine compound of claims 13–15 to that of claims 1–11 is from the range of 1:00 to 100:1 in mole ratio, more preferably from 10:1 to 1:10, especially preferably is from 3:1 to 1:3. As hydrazine compounds employed in the present invention, other than the compounds described above, those described below may also be employed. The compounds include those described in Research Disclosure, Item 23516 (November 1983 Issue, page 345) and publications cited therein, listed can be those described in U.S. Pat. Nos. 4,080,207, 4,269,929, 4,276,364, 4,278,748, 4,385,108, 4,459,347, 4,478,928, 4,560,638, 4,686,167, 4,912,016, 4,988,604, 4,994,365, 5,041,355, and 5,104,769; U.K. Patent No. 2,011,391B; European Patent Nos. 217310, 301, 799, and 356,898; and JP-A Nos. 60-179734, 61-170733, 61-270744, 62-178246, 62-270948, 63-29751, 63-32538, 63-104047, 63-121838, 63-129337, 63-223744, 63-234244, 63-234245, 63-234246, 63-294552, 63-306438, 64-10233, 1-90439, 1-100530, 1-105941, 1-105943, 1-276128, 1-280747, 1-283548, 1-283549, 1-285940, 2-2541, 2-77057, 2-139538, 2-196234, 2-196235, 2-198440, 2-198441, 2-198442, 2-220042, 2-221953, 2-221954, 2-285342, 2-285343, 2-289843, 2-302750, 2-304550, 3-37642, 3-54549, 3-125134, 3-184039, 3-240036, 3-240037, 3-259240, 3-280038, 3-282536, 4-51143, 4-56842, 4-84134, 2-230233, 4-96053, 4-216544, 5-45761, 5-45762, 5-45763, 5-45764, 5-45765, 6-289524, and 9-160164, etc.

Furthermore, other than those, employed can be compounds described in (Chem 1) of JP-B No. 6-77138, specifically, compounds described on pages 3 and 4 of the Publication; compounds represented by general formula (I) in JP-B No. 6-93082, specifically, compounds 1 through 38 described on pages 8 to 18 of the Publication; compounds represented by general formula (4), general formula (5), and general formula (6) in JP-A No. 6-230497, specifically, compounds 4-1 through 4-10 on pages 25 and 26, compounds 5-1 through 5-42 on pages 28 to 36, and compounds 6-1 through 6-7 on pages 39 and 40 of the Publication; compounds represented by general formula (I) and general formula (2) in JP-A No. 6-289520, specifically, compounds 1-1) through 1-17) and 2-1) on pages 5 to 7 of the Publication; compounds described in (Chem 2) and (Chem 3) of JP-A No. 6-313936, specifically, compounds described on pages 6 to 19 of the Publication; compounds described in (Chem 1) of JP-A No. 6-313951, specifically, compounds described on pages 3 to 5 of the Publication; compounds represented by general formula (I) in JP-A No. 7-5610, specifically, compounds I-1 through I-38 described on pages 5 to 10 of the Publication; compounds represented by general formula (II) in JP-A No. 7-77783, specifically, compounds II-1 through II-102 described on pages 10 to 27 of the Publication; and compounds represented by general formula (H) and general formula (Ha) in JP-A No. 7-104426, specifically, compounds H-1 through H-44 described on pages 8 to 15 of the Publication.

It is preferable to use an amine compound represented by the following general formula (Na) or (Nb).

Formula (Na)

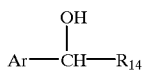

Formula (Nb)

In the formula (Na), R11, R12 and R13 independently represent a hydrogen atom, an alkyl group, a substituted alkyl group, an alkenyl group, a substituted alkenyl group, an alkynyl group, an aryl group or a substituted aryl group, provided that R11, R12 and R13 can combine with each other to form a ring. Among the compounds represented by formula (Na) is preferable an aliphatic tertiary amine compound. It is preferable for these compounds to contain in their molecules a diffusion-proof group or a silver halide-adsorption-promoting group. In order to be non-diffusible, the compound has preferably a molecular weight of not less than 100, and more preferably, a molecular weight of not less than 300. Preferred adsorption-promoting groups include a heterocyclic group, a mercapto group, a thioether group, a thione group, and a thiourea group.

Particularly preferred compound represented by the general formula (Na) include a compound having in its molecule at least one thioether group as the silver halide adsorption-promoting group.

Exemplary nucleation accelerating compounds represented by formula (Na) are given below.

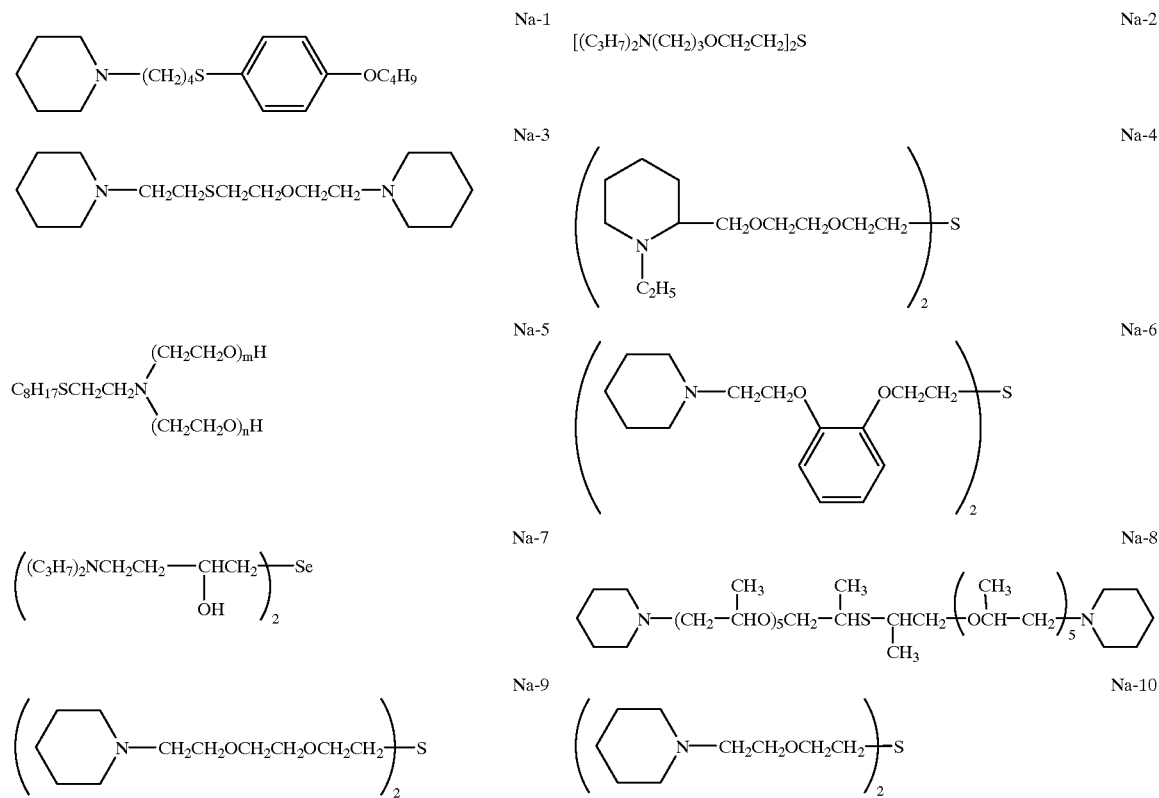

-continued

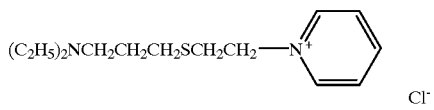
Na-11

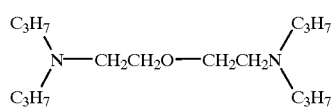
Na-13

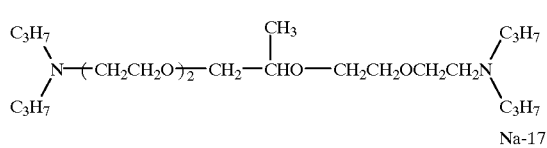
Na-15

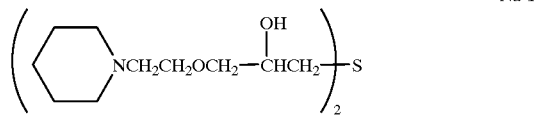
Na-17

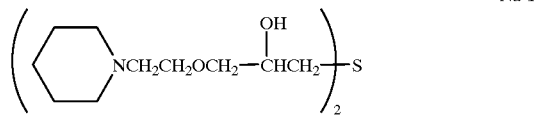
Na-19

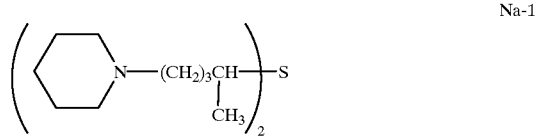
Na-21

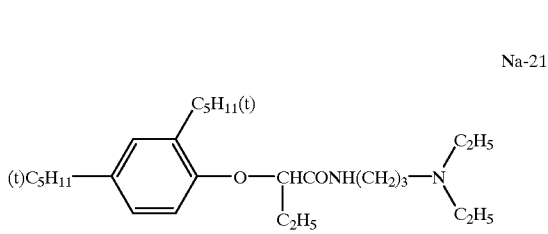
Na-23

Na-25

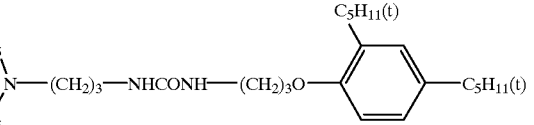
Na-27

Na-12

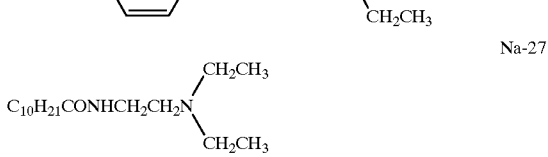

In formula (Nb), Ar represents a substituted or unsubstituted aromatic hydrocarbon group or a heterocyclic group. R14 represents a hydrogen atom, an alkyl group, an alkenyl group, an alkynyl group, or an aryl group, provided that Ar and R14 may be linked to form a ring. The compound preferably contains in its molecule a diffusion-proof group or a silver halide adsorption-promoting group. The molecular weight to confer diffusion-proof property on the compound is 120 or more, and, more preferably, 300 or more. Further, preferred silver halide adsorption-promoting groups are the same as defined in the formula (H).

In addition, specific examples of the nucleation accelerating compounds include exemplified Compounds (2-1) through (2-20) disclosed in Japanese Patent OPI Publication No. 6-258751(1994) and exemplified Compounds 3-1 to 3-6 disclosed in JP-A 6-258751.

The amine compounds may be used in any layer located on the side of the silver halide emulsion layer. Preferably the compounds are incorporated either in the silver halide emulsion layer or a layer adjacent thereto. The optimal addition amount may be varied depending on the size, halide composition, degree of chemical ripening of silver halide grains and kind of restraining agent used, however, it is preferably between 10-6 and 10-1 mol, and more preferably between 10-5 and 10-2 mol per one mol of silver halide.

The silver halide photographic light sensitive material of the invention is described in detail. The silver halide photographic light sensitive material to which the hydrazine compound according to the invention is contained is preferably black and white silver halide photographic light sensitive material, more preferably the silver halide photographic light sensitive material for preparation of printing plate.

The composition of the silver halide of the silver halide emulsion contained in the silver halide photographic photosensitive material of the invention is preferably silver chlorobromide containing not less than 60 mol % silver chloride or silver chloroiodobromide containing not less than 60 mol % silver chloride. Preferable average grain size of the silver halide is not more than 0.7 $\mu$m, particularly preferably 0.5 to 0.1 $\mu$m. The average grain size is usually employed by specialist in the photographic science and is readily understood. The term grain size is usually refers to as diameter of the grain, when the grain is of spherical shape or in the form close thereto.

In the case when the grain is a cubic shape, it means as average diameter of a sphere when the cube is converted into a sphere having the equivalent volume. With regard to the method of obtaining the average diameter, one can refer to the disclosure on pages 36–43, third edition of "the theory of the photographic process" edited by C. E. Mees and T. H. James and published by Mcmillan Co. in 1966.

There is no limitation as to the shape of the silver halide grain, and any one of tabular, cubic, spherical, tetradecahedral or octahedral shape can optionally be used. Concerning grain size distribution, the narrower, the more preferable. Particularly, so-called mono-dispersed emulsion, in which more than 90%, preferably 95%, of the total number of grains fall in the range ±40% around the average grain size, is preferable. A method for mixing soluble silver halide and soluble halogen salt in the invention may include any of a single-sided mixing method, a simultaneous mixing method a combination thereof. It is also possible to use a method (so-called reverse precipitation method) in which grains are formed under the condition of excessive silver ions. As a type of double-jet methods, it is possible to use a method to keep the pAg constant in a liquid phase in which silver halides are produced, namely the so-called controlled double jet method. Owing to this method, it is possible to obtain a silver halide emulsion in which crystal shapes are regular and grain diameters are almost uniform. It is preferred to add zinc salt, lead salt, thallium salt, iridium salt, rhodium salt, ruthenium salt, or osmium salt, or complex salt containing the element of these salt to the silver halide grains employed in the silver halide emulsion during the formation of the grains or at least one of processes of growing the grains. Generally known sulfur sensitization, reduction sensitization or noble metal sensitization may be employed in combination with the sensitization using selenium, tellurium compound etc. As for the sulfur sensitizers, besides sulfur compounds contained in gelatin, various sulfur compounds, for example, thiosulfates, thioureas, rhodanines, polysulfide compounds, etc. can be used. The gold sensitization, which is representative among the noble metal sensitization, employs mainly gold complex salt. Complex salt of the noble metal other than gold, for example, platinum, palladium, rhodium etc. may be contained. For the reduction sensitization stannous salts, amines, formamidinesulfinic acid, silane compounds may be employed.

Silver halide emulsion and a method of its preparation are described in Research Disclosure, vol. 176, 17643, pages 22–23 (December 1978) or references cited therein in detail.

Various compounds may be added for the purpose of preventing fog during manufacturing process, storage or development process or stabilizing photographic characteristics of the photosensitive material of the invention. The following compounds known as an ant-foggant or stabilizer can be added. Examples are azoles such as benzothiazolium salts, nitro indazoles, nitrobenzimidazoles, chlorobenzimidazoles, bromobenzimidazoles, mercaptothiazoles, mercaptobenzthiazoles, mercaptobenzimidazoles, mercaptothiadiazoles, aminotriazoles, benzotriazoles, nitrobenzotriazoles, mercaptotetrazoles, particularly (1-phenyl-5-mercapto tetrazole; mercapto-pyrimidines, mercaptotriazines; azaindenes such as triazaindenes, tetrazaindenes in particular 4-hydroxy-substituted-1,3,3a,7-tetrazaindenes, pentazaindenes; benzenthiosulfonic acids, benzenesulfinic acids and benzenesulfonic acid amides.

Desensitizing method employing organic desensitizer other than the desensitization by metal doping in the present invention.

Specific organic desensitizers usable in the present invention are given below.

(1) Phenosafranine
(2) Pinakryptol green
(3) 2,3-Dimethyl-6-nitro-benzthiazolium p-toluene sulfonate
(4) 2-(p-nitrostyryl)quinoline p-toluene sulfonate
(5) 1,3-Diethyl-1-methyl-2-phenylimidazo-(4,5-b) quinoxaline-3-indocarbocyanine iodide
(6) Pinakryptol yellow
(7) 1,1,3,3-Hexamethyl-5,5-dinitroindo-carbocyanine p-toluene sulfonate
(8) 5,5-Dichloro-3,3-diethyl-6,6-dinitro-carbocyanine iodide
(9) 1,1-Dimethyl-2,2-diphenyl-3,3-indoro-carbocyanine bromide The amount of use of the above-mentioned desensitizing agent is usually between 10 mg to 5 g per 1 mol of silver halide, and, more preferably, 50 mg to 3 g. It may be incorporated in the form of an aqueous solution or a solution of an organic solvent. Further it may also be incorporated in the form of a dispersion of solid fine particles prepared by mean of a sand mill, a ball-mill or impeller dispersion. The particle size is usually appropriate within a range of 0.001 to 20 $\mu$m. Particularly preferable size is 0.01 to 1 $\mu$m.

The organic desensitizing agent is often characterized in terms of polarographic half-wave potential. That is to say, the sum of anodic potential and cathodic potential in the polarograph is positive. The measurement thereof is disclosed in the U.S. Pat. No. 3,501,307.

Various known surfactants may be employed in colloidal layer of the light sensitive emulsion layer and/or non-light sensitive layer according to the invention for various purpose such as coating aid, antistatic purpose, improving lubrication, emulsifying, preventing adhesion and improvement of photographic characteristics. As binder or a protective colloid of the photographic emulsion used in the present invention, gelatin is advantageously used, however, other hydrophilic colloids may also be used. The hydrophilic colloids include, for example, gelatin derivatives, graft polymers comprised of gelatin and other polymers; proteins such as casein, albumin, etc.; cellulose derivatives such as hydroxyethyl cellulose, carboxymethyl cellulose, cellulose sulfates, etc.; sugar derivatives such as sodium alginate, starch derivatives, etc.; synthetic hydrophilic polymers such as polyvinyl alcohol and partial acetal thereof, poly-N-pyrrolidone, polyacrylic acid, polymethacrylic acid, polyacrylamide, polyvinyl imidazole, polyvinyl pyrazole, etc. These polymers may be either homopolymers or copolymers.

As gelatin, there may be usable an acid process gelatin as well as lime-processed gelatin. Further, hydrolytic products or enzyme decomposition products of gelatin may also be used.

In the photographic emulsion according to the present invention, for the purpose of improving dimensional stability, etc., synthetic polymers, which are water-insoluble or sparingly water-soluble, can be incorporated. For example, alkyl(metha) acrylates, alkoxy (metha) acrylates, glycidyl (metha) acrylates, (metha)acrylamides, vinyl esters such as vinyl acetate, acrylonitrile, styrene, etc. may be used either singly or in combination. Further, these polymers may be used in the form of a copolymer together with other monomer constituents such as acrylic acid, methacrylic acid, α,β-unsaturated dicarboxylic acid, hydroxylalkyl(metha)acrylate, sulfoalkyl(metha)acrylate, styrene sulfonic acid, etc.

As to other conventional additives, various additives such as desensitizing agent, plasticizer, lubricant, development accelerator, and oil may be employed. As for the additives and those mentioned above the compounds disclosed in Research Disclosure Nos. 17643 (December 1978), 18716 (November 19798) and 30811 (December 1989) can be mentioned. Below, compounds disclosed in these three references and locations thereof are given.

Each of the emulsion layer and the protective layer may be composed of a single layer or multiple layers composed of plural layers in the light sensitive material of the present invention. In case of multiple layers inter layer etc. may be provided.

Support for the light sensitive material is flexible support, on one side or both sides of which are coated.

As an anti-silver-slugging agent, may be incorporated an anti-silver-stain agent as disclosed in JP-A Nos. 3-51844, 4-26838, 4-362942, and 1-319031. Particularly the compounds represented by the following formula SL are preferable. SL

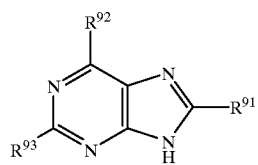

In the formula, $R^{91}$, $R^{92}$ and $R^{93}$ each represents a hydrogen atom, an —$SM_1$, hydroxy, lower alkoxy, —$COOM_2$, amino, —$SO_3M_3$ or lower alkyl group, with proviso that at least one of $R^{91}$, $R^{92}$ and $R^{93}$ is —SM1. $M_1$, $M_2$ and $M_3$ each represents a hydrogen atom, alkali metal atom or an ammonium group, which may be same or different. The lower alkyl group and the lower alkoxy group represented by $R^{91}$, $R^{92}$ and $R^{93}$ have 1 to 5 carbon atoms. The amino group represented by $R^{91}$, $R^{92}$ and $R^{93}$ represents a non-substituted or substituted amino group. Preferable example of $R^{91}$, $R^{92}$ and $R^{93}$ is a lower alkyl group. The ammonium group in the formula SL is a non-substituted or substituted ammonium group, preferably a non-substituted ammonium group.

Specific examples of compounds represented by formula SL are shown below.

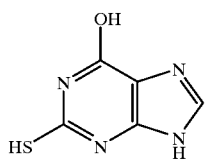

SL-1

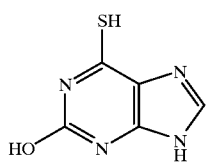

SL-2

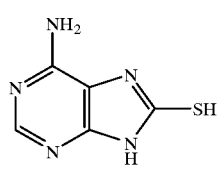

SL-3

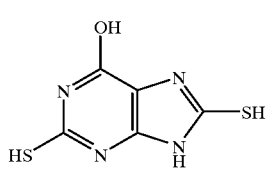

SL-4

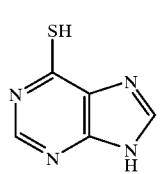

SL-5

It is preferred to employ an anti-halation dye, particularly, a dye dispersed in a form of solid particles dyes for the improvement of image sharpness.

As the dye to be dispersed to the solid particles, a compound represented by Formula I to VI is preferably used.

[I]

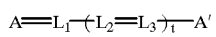

[II]

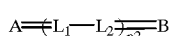

[III]

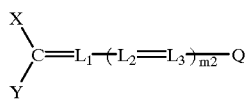

[IV]

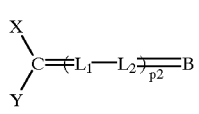

[V]

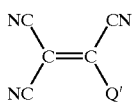

[VI]

In the formulae, A and A' are each an acidic nucleus which may be the same or different, and B is a basic nucleus, Q' is a heterocyclic group, $X_4$ and $Y_1$ are each an electron withdrawing group which may be the same or different, and $L_1$, $L_2$ and $L_3$ are each a methine group. $m_2$ is 0 or 1, t is 0, 1 or 2, and p2 is 0 or 1. The dyes represented by formulae I to VI each have at least one group selected from a carboxyl group, sulfonamide group and a sulfamoyl group in the molecular thereof.

As the acidic nucleus represented by A or A' in Formulae I, II and III, a nucleus of 5-pyrazolone, barbituric acid, thiobarbituric acid, rhodanine, hydantoin, thiohydantoin, oxazolone, isooxazolone, indandione, pyrazolidinedione, oxazolinedione, hydroxypyridone and pyrazolipyridone are preferably cited.

As the basic nucleus represented by B in Formulas III and V, a nucleus of pyridine, quinoline, benzoxazole, naphthoxazole, thiazole, benzothiazole, naphthothiazole, indolenine, pyrrole and indole are preferably cited.

As the aryl group represented by Q in Formulas I and IV, a phenyl group and a naphthyl group are cited. The heterocyclic group represented by Q or Q' in Formula I, IV and VI include, for example, a pyridyl group, a quinolyl group, an isoquinolyl group, a pyrrolyl group, a pyrazolyl group, an imidazolyl group, an indolyl group, a furyl group and a thienyl group. The aryl group and the heterocyclic group include ones having a substituent. As the substituent, an alkyl group having 1 to 8 carbon atoms such as a methyl group, ethyl group, t-butyl group, octyl group, 2-hydroxyethyl group and 2-methoxyethyl group, a hydroxy group, a cyano group, a halogen atom such as a fluorine atom and chlorine atom, an alkoxy group having 1 to 6 carbon atoms such as a methoxy group, ethoxy group, 2-hydroxyethoxy group, methylenedioxy group and butoxy group, a substituted amino group such as a dimethylamino group, diethylamino group, di(n-butyl)amino group, N-ethyl-N-hydroxyethylamino group, N-ethyl-N-methanesulfonamidoethylamino group, morpholino group, piperidino group and pyrrolidino group, a carboxyl group, a sulfonamido group such as a methanesulfonamido group and benzenesulfonamido group and a sulfamoyl group such as a sulfamoyl group, methylsulfamoyl group and phenylsulfamoyl group are preferred, these substituents may be applied in combination.

The electron withdrawing groups represented by X and Y in Formula IV and V may be the same or different and ones having a Hammett s substituent constant _p, described in "Relation of Structural Activity of Medicine" Extra Number 122 of Kagaku no Ryoiki (Area of Chemistry) edited by Fujita, p.p. 96–103, 1979, of not less than 3.0 are preferred, which include, for example, a cyano group, an alkoxycarbonyl group such as a methoxycarbonyl group, ethoxycarbonyl group, butoxycarbonyl group and octyloxycarbonyl group, an aryloxycarbonyl group such as a phenoxycarbonyl group and 4-hydroxyphenoxycarbonyl group, a carbamoyl group such as a carbamoyl group, dimethylcarbamoyl group, phenylcarbamoyl group and 4-carboxyphenylcarbamoyl group, an acyl group such as a methylcarbonyl group, ethylcarbonyl group, butylcarbonyl group, phenylcarbonyl group and 4-ethylsulfonamidocarbonyl group, an alkylsulfonyl group such as a methylsulfonyl group, ethylsulfonyl group, butylsulfonyl group and octylsulfonyl group and an arylsulfonyl group such as a phenylsulfonyl group and 4-chlorophenylsulfonyl group.

The methine group represented by L1, L2 and L3 on Formulas I to V include ones having a substituent. As the substituent, for example, an alkyl group having 1 to 6 carbon atoms such as a methyl group, ethyl group and hexyl group, an aryl group such as a phenyl group, tolyl group and 4-hydroxyphenyl group, an aralkyl group such as a benzyl group and phenetyl group, a heterocyclic group such as a pyridyl group, furyl group and thienyl group, a substituted amino group such as a dimethylamino group, diethylamino group and anilino group and an alkylthio group such as a methylthio group are cited.

In the invention, among the dyes represented by Formula I to VI, ones having at least one carboxyl group in the molecule thereof are preferable, and dyes represented by Formula I is more preferred and ones represented by Formula I in which Q is a furyl group are particularly preferred.

Concrete examples of preferably usable dye are shown below, however, the dye is not limited thereto.

AD-1
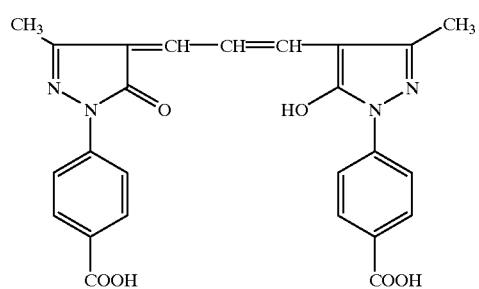

AD-2
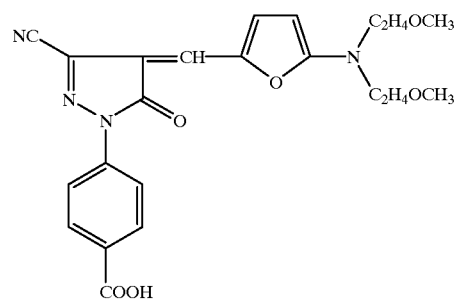

AD-3
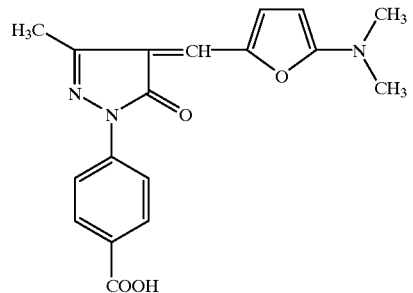

AD-4
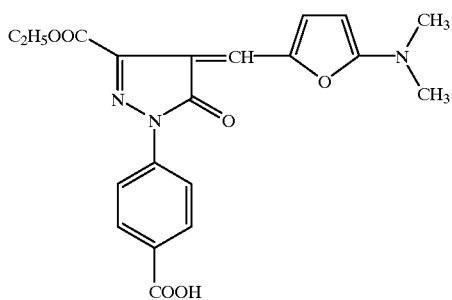

AD-5
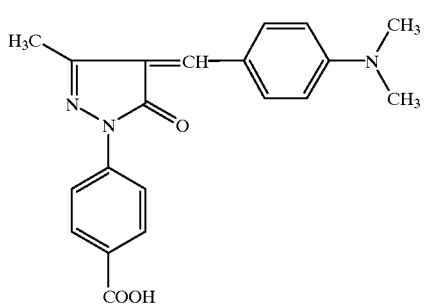

AD-6
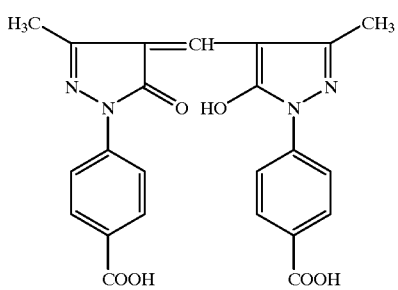

AD-7
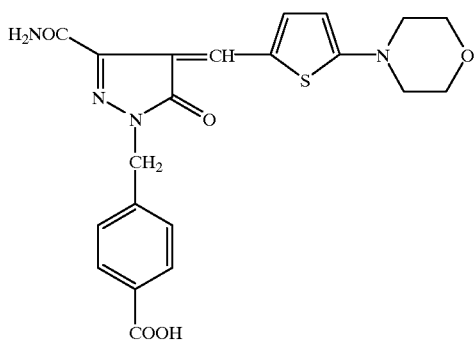

AD-8
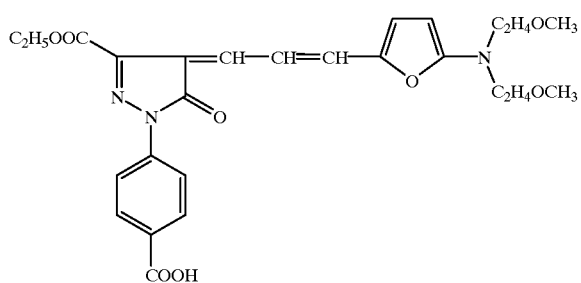

AD-9
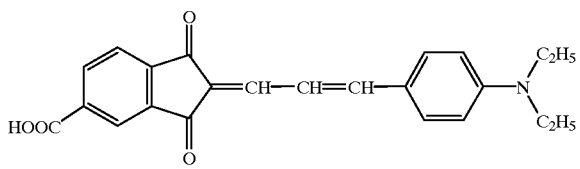

AD-10
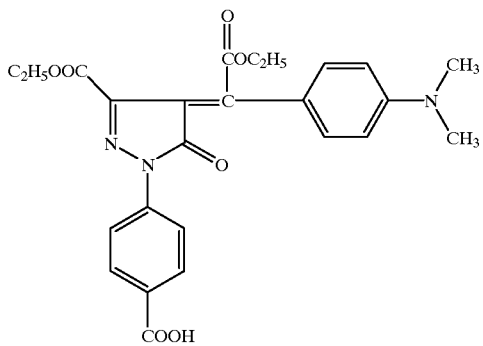

AD-11
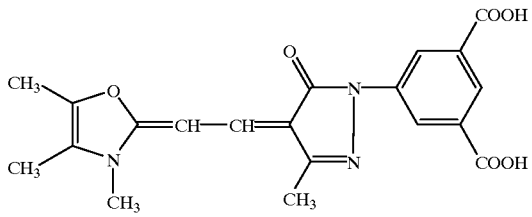

AD-12
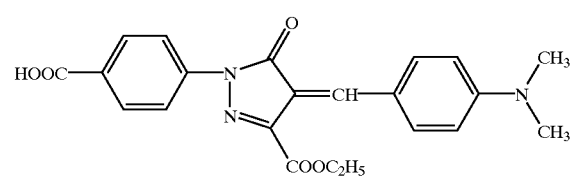

As preferable examples of the compound represented by Formula I to VI other than the above-mentioned, for example, Compound Nos. 1-1 to I-30, II-1 to II-12, III-1 to III-8, IV-1 to IV-9, V-1 to V-8 and VI-1 to VI-5 described in JP Application No. 5-277011, pp. 19–30 and JP-A No. 7-128793 are cited.

The methods described in JP-A. Nos. 52-92716, 55-155350, 55-155351, 63-197943 and 3-182743 and WO88/04794 can be applied to prepare the dispersion of solid particle of dye relating to the invention.

In concrete, the dispersion can be prepared by means of a fine dispersing machine such as a ball mill, planet mill, vibration mill, sand mill, roller mill, a jet mill and disk impeller mill. Furthermore, the dispersion of the compound can be prepared by a method by which the compound is dissolved in weak alkaline water and then the pH of the solution is lowered to a weak acidity to precipitate the compound in a form of fine solid particles or a method by which an weak alkaline solution of the compound and an acidic water are mixed by a double-jet method to precipitate fine solid particles of the compound, when the compound to be dispersed to solid particles is water-insoluble at a relative low pH and water-soluble at a relative high pH.

The dispersion of solid particle of the dye may be use singly or in combination of two or more kinds. The dispersion may be used as a mixture of a dispersion of compound other than that of the invention. When two or more kinds of compounds are used in combination, the compounds may be mixed after dispersed separately or may be dispersed simultaneously. It is preferred to add a surfactant during or after dispersing process when the dispersion of solid particles of dye is prepared in the presence of an aqueous medium. Although an anionic surfactant, a nonionic surfactant, a cationic surfactant and an amphoteric surfactant may also be used as the surfactant, an anionic surfactant such as alkylsulfonates, alkylbenzenesulfonates, alkylnaphthalenesulfonates, alkyl sulfates, sulfosuccinates, sulfoalkylpolyoxyethylenealkylphenyl ethers and N-acyl-N-alkyltaurines, and a nonionic surfactant such as saponin, alkyleneoxide derivatives and alkyl esters of sugar, are preferred. The above-mentioned anionic surfactants are particularly preferred. As concrete examples of the surfactant, Compounds 1 to 32 described on page 32 to 46 of JP-A No.7-128793 are cited, the surfactant is not limited thereto. The using amount of the anionic and/or nonionic surfactant is usually 0.1 mg to 2000 mg, preferably 0.5 mg to 1000 mg, per gram of the dye even though the amount is varied depending on the kind of surfactant or the dispersing condition of the dispersing liquid medium.

The concentration of the dye in the dispersion is 0.01% to 50%, preferably 0.1% to 30%, by weight. The surfactant is preferably added at a step before the start of dispersion, and may be further added after completion of the dispersion according to necessity. The anionic and/or nonionic surfactant may be used singly or in combination of two or more kinds including a combination of both of the anionic and nonionic ones.

The solid particle dispersion of the dye is preferably dispersed so that the average diameter is 0.01 μm to 5 μm, more preferably 0.01 μm to 1 μm, particularly preferably 0.01 μm to 0.5 μm. The variation coefficient of the particle size distribution of the dispersed solid particles is preferably not more than 50%, more preferably not more than 40%, further preferably not more than 30%. The variation coefficient of the particle size distribution is a value determined by the following equation.

(Standard deviation of particle diameter)/(Average of particle diameter)×100

A hydrophilic colloid to be used as the binder of a photographic constituent layer may be added to the solid particle dispersion of the invention before the start or after completion of dispersing process. Although gelatin is advantageously used as the hydrophilic colloid, another hydrophilic colloid, for example, a gelatin derivative such as phenylcarbamyl gelatin, acylated gelatin and phthalated gelatin, a graft-polymer of gelatin and a monomer having a methylene group capable of polymerizing with gelatin, a cellulose derivative such as carboxymethyl cellulose, hydroxymethyl cellulose and cellulose sulfate, a hydrophilic polymer such as polyvinyl alcohol, partially oxide polyvinyl acetate, polyacrylamide, poly-N-,N-dimethylacrylamide, poly-N-vinylpyrrolidone and polymethacrylic acid, agar, gum arabic, alginic acid, albumin and casein are also usable. Two or more kinds of the hydrophilic colloid may be used in combination. The adding hydrophilic colloid to be added to the solid particle dispersion is preferably 0.1% to 12%, more preferably 0.5% to 8%, by weight.

The solid particle dispersion of the dye is preferably added to a layer constituting the photographic material such as a light-sensitive emulsion layer, upper emulsion layer, lower emulsion layer, protective layer, subbing layer of the support or backing layer. It is particularly preferred for enhancing the anti-halation effect to add the dispersion into a layer provided between the support and the emulsion layer or a constituent layer provided on the side of the support opposite to the emulsion coated side. For enhancing the effect on the resistivity against safelight, the solid particle dispersion is preferably added to a layer provided on the emulsion layer.

The preferable adding amount of the solid particle dispersion of the dye is 1 mg to 1 g, preferably 5 to 800 mg, more preferably 10 mg to 500 mg, per square meter of the light-sensitive material, which may be varied depending on the kind of the dye or the property of the photographic light-sensitive material.

The present invention may have a light sensitive emulsion layer containing a dye dispersed in solid state between the support and a light sensitive emulsion layer, and other light sensitive and non-light sensitive layer or non-emulsion layer (hydrophilic colloid layer, hydrophobic polymer layer) may contain a dye dispersed in solid state. Further, any layers on opposite side with reference to the support may contain. Any layer may contain a water soluble dye in addition thereto.

The amount of the dye dispersed in solid state is preferably such that obtaining light absorption density of 0.001 to 2.0, in particular preferably 0.005 to 1.5 in a range at least a part of wave length of light source employed for exposure. A dye having other absorption wave length may employed in combination in any layer.

A hardening agent represented by the following formula (F) is preferably used.

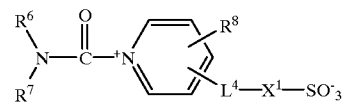

In the general formula (F), $R^6$, and $R^7$ independently represent straight chain, branched or a cyclic alkyl group having 10 to 20 carbon atoms, for example, methyl group, ethyl group, butyl group, cyclohexyl group, 2-ethylhexyl group, dodecyl group, etc.; an aryl group of 6 to 20 carbon atoms such as phenyl group, naphthyl group, etc. can be mentioned. Further, it is also preferable that $R^6$ and $R^7$ is combined with each other to form a ring together with a nitrogen atom, and especially preferable rings are a morpholine ring or a pyrrolidine ring. $R^8$ represents a hydrogen atom or a substituent whose example is such as listed for a substituent of aryl group or heterocycle group above, and hydrogen atom is particularly preferable. $L^4$ represents not only a single bond but also an alkylene group with 1 to 20 carbon atoms, such as methylene group, ethylene group, trimethylene group, propylene group; or an arylene group with 6 to 20 carbon atoms, for example, phenylene group, and a divalent group obtained by combining these groups such as p-xylene group; an acylamino group, such as —NHCOCH$_2$—, sulfonamide group such as —NHSO$_2$CH$_2$— can be mentioned. Preferably, it is a single bond, an alkylene group such as methylene group and ethylene group, or an acylamino group. $X^1$ represents a single bond, —O— or —N($R^9$)—, in which $R^9$ is a hydrogen atom, an alkyl group with 1 to 20 carbon atoms, such as methyl group, ethyl group, benzyl group; or an aryl group of carbon atoms of 6 to 20, such as phenyl group, or an alkoxy group of 1 to 20 carbon atoms, such as methoxy group, and among these, hydrogen atom is particularly preferable.

Laser light source employed in the invention is described in detail. Exposure to the photosensitive material of the present invention is preferably carried out using an Ar laser (488 nm), a He—Ne laser (633 nm), a red color semiconductor laser (670 nm), an infrared semiconductor laser (780 nm and 830 nm), etc.

In the silver halide photosensitive material of the present invention, employed can be sensitizing dyes described, for example, in JP-A Nos. 63-159841, 60-140335, 63-231437, 63-259651, 63-304242, and 63-15245; U.S. Pat. Nos. 4,639, 414, 4,740,455, 4,741,966, 4,751,175, and 4,835,096. Useful sensitizing dyes employed in the present invention are described, for example, in publications described in or cited in Research Disclosure Items 17643, Section IV-A (page 23, December 1978), 1831, Section X (page 437, August 1978). Particularly, selected can advantageously be sensitizing dyes having the spectral sensitivity suitable for spectral characteristics of light sources of various types of scanners. For example, dyes are preferably selected from: A) for an argon laser, simple merocyanines described in JP-A Nos. 60-162257 and 2-48653; U.S. Pat. No. 2,161,331; West Germany Patent No. 930,071; and JP-A No. 5-11389; B) for helium-neon laser, tri-nucleus cyanine dyes illustrated in JP-A Nos. 50-62425, 54-18726, and 59-102229, and merocyanines illustrated in Japanese Patent Application 6-103272; C) for a LED light source and a red semiconductor laser, thiacarbocyanine described in JP-B Nos. 48-42172, 51-9609, 55-39818; and JP-A Nos. 62-284343 and 2-105135; D) for an infrared semiconductor laser light source, tricarbocyanines described in JP-A Nos. 59-191032 and 60-80841, and dicarbocyanines containing a 4-quinoline nucleus described in general formulas (IIIa) and (IIIb) in JP-A Nos. 59-192242 and 3-67242. These sensitizing dyes may be individually or in combinations thereof. The combinations of sensitizing dyes are frequently for the purpose of supersensitization. Sensitizing dyes described in JP A 4-182639 and 5-341432, JP B 6-52387 and 3-10931, U.S. Pat. No. 5,441,866, and JP A 7-13295 are preferably employed in response to laser source having long wave length area such as 750 nm or more, particularly 800 nm or more. These sensitizing dyes may be individually or in combinations thereof. The combinations of sensitizing dyes are frequently for the purpose of supersensitization. The compounds which exhibit no spectral sensitizing action or substantially absorb no visible light and exhibit supersensitization may be incorporated into an emulsion.

The development processing is described in detail below.

It is one of the preferable development processing to process employing an automatic processor comprising four processes of developing, fixing, rinsing (or stabilizing) and drying in the present invention.

Known developing agent is employed in the present. Examples of the developing agent usable in the invention include dihydroxybenzenes (e.g., hydroquinone, hydroquinone-monosulfonate), 3-pyrazolidones (e.g., 1-phenyl-3-pyrazolidone, 1-phenyl-4-methyl-3-pyrazolidone, 1-phenyl-4,4-dimethyl-3-pyrazolidone, 1-phenyl-4-ethyl-3-pyrazolidone, 1-phenyl-5-methyl-3-pyrazolidone), aminophenols (e.g., o-aminophenol, p-aminophenol, N-methyl-o-aminophenol, N-methyl-p-aminophenol, 2,4-diaminophenol), ascorbic acid and its salts (e.g., ascorbic acid sodium ascorbate, potassium ascorbate, erythorbic acid), metal complex salts (e.g., Fe-EDTA, Fe-DTPA, Ni-DTPA). These are used in singly or in combination.

In particular, the present invention is characterized by image forming method by employing developer containing a developing agent represented by the following formula A.

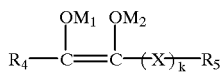

Formula (A)

In Formula (A), $R_4$ and $R_5$ each independently represents a substituted or an unsubstituted alkyl group, a substituted or an unsubstituted amino group, a substituted or an unsubstituted alkoxy group, and a substituted or an unsubstituted alkylthio group, and $R_4$ and $R_5$ may be linked with together to form ring, k is 0 or 1, and X is —CO— or —CS— when k is 1, and $M_1$ and $M_3$ are each a hydrogen atom or an alkali metal atom.

Among the compound represented by the formula (A), the following compound represented by the formula (A-a) in which $R_4$ and $R_5$ are linked with together to form ring is especially preferable.

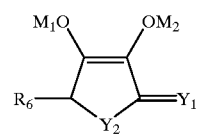

Formula (A-a)

In Formula, $R_6$ represents a hydrogen atom, a substituted or an unsubstituted alkyl group, a substituted or an unsubstituted aryl group, a substituted or an unsubstituted amino group, a substituted or an unsubstituted alkoxy group, a sulfo group, a carboxyl group, an amide group and a sulfonamide group, $Y_1$ represents O or S, $Y_2$ represents O, S or $NR_7$, $R_7$ represents a substituted or an unsubstituted alkyl group, and a substituted or an unsubstituted aryl group, and $M_1$ and $M_2$ are each a hydrogen atom or an alkali metal atom.

As an alkyl group in Formula (A) or Formula (A-a), is preferably cited a lower alkyl group having 1 to 5 carbon atoms, as an amino group is preferably cited an unsubstituted amino group or an amino group substituted by a lower alkyl group, as an alkoxy group is preferably cited a lower alkoxy group, as an aryl group is preferably cited a phenyl group or a naphthyl group which may possess substituents such as a hydroxyl group, a halogen atom, an alkoxy group, a sulfo group, a carboxyl group, an amide group and a sulfonamide group.

Examples of the compound represented by Formula (A) or Formula (A-a) are shown below.

| Formula (A) | | | | | |
|---|---|---|---|---|---|
| Compound No. | X | $R_4$ | $R_5$ | $M_1$ | $M_2$ |
| A-1 | — (k = 0) | $HOCH_2-CH(OH)-CH(OH)-$ | $-OH$ | H | H |
| A-2 | — (k = 0) | $CH_3-CH(OH)-CH(OH)-$ | $-OH$ | H | H |
| A-3 | — (k = 0) | $HOCH_2-CH(OH)-CH(OH)-$ | $-CH_3$ | H | H |
| A-4 | — (k = 0) | $CH_3-CH(OH)-CH(OH)-$ | $-CH_3$ | H | H |
| A-5 | $-C(=O)-$ (k = 1) | $HOCH_2-CH(OH)-CH(OH)-$ | $-OH$ | H | H |
| A-6 | $-C(=O)-$ (k = 1) | $CH_3-CH(OH)-CH(OH)-$ | $-OH$ | H | H |
| A-7 | $-C(=S)-$ (k = 1) | $HOCH_2-CH(OH)-CH(OH)-$ | $-OH$ | H | H |
| A-8 | $-C(=S)-$ (k = 1) | $CH_3-CH(OH)-CH(OH)-$ | $-OH$ | H | H |
| A-9 | $-C(=O)-$ (k = 1) | $HO-CH_2-$ | $-OH$ | Na | H |
| A-10 | $-C(=O)-$ (k = 1) | $HO-CH_2-$ | $-CH_3$ | H | H |
| A-11 | $-C(=O)-$ (k = 1) | $HO-CH_2-$ | $-C_2H_5$ | H | H |
| A-12 | $-C(=O)-$ (k = 1) | $HO-CH_2-$ | $-C_2H_4OH$ | H | Na |

| Formula (A-a) | | | | | |
|---|---|---|---|---|---|
| Compound No. | $Y_1$ | $Y_2$ | $R_6$ | $M_1$ | $M_2$ |
| A-13 | O | O | H | H | H |
| A-14 | O | O | $CH_3$ | H | H |
| A-15 | O | O | $-CH_2OH$ | H | H |
| A-16 | O | O | $CH_3-CH(OH)-$ | H | H |
| A-17 | O | O | $HOCH_2-CH(OH)-$ | H | H |

-continued

Formula (A-a)

| Compound No. | $Y_1$ | $Y_2$ | $R_6$ | $M_1$ | $M_2$ |
|---|---|---|---|---|---|
| A-18 | O | O | HOCH$_2$—CH—<br>\|<br>OH | Na | H |
| A-19 | O | O | HOOCCH$_2$—CH—<br>\|<br>OH | H | Na |
| A-20 | S | O | H | Na | H |
| A-21 | S | O | CH$_3$—CH—<br>\|<br>OH | H | H |
| A-22 | S | O | HOCH$_2$—CH—<br>\|<br>OH | H | H |
| A-23 | O | NCH$_3$ | H | H | H |
| A-24 | O | NH | HOCH$_2$—CH—<br>\|<br>OH | H | K |
| A-25 | O | S | H | H | H |
| A-26 | O | S | HOCH$_2$—CH—<br>\|<br>OH | H | H |
| A-27 | O | S | CH$_3$—CH—<br>\|<br>OH | H | H |
| A-28 | S | S | H | H | H |
| A-29 | S | S | HOCH$_2$—CH—<br>\|<br>OH | H | H |
| A-30 | S | S | H | H | H |

These compounds are representatively ascorbic acid and erythorbic acid, and their salts, or derivatives derived therefrom, and they are commercially available or easily synthesized according to known synthetic method.

The developing agent referred to here is a compound which occupies 50% or more in mol among the compounds capable of developing silver halide in the developer In the present invention, the combined usage of the developing agent consisting of the ascorbic acid and its derivative together with the developing agent consisting of 3-pyrazolidone derivative (e.g., 1-phenyl-3-pyrazolidone, 1-phenyl-4-methyl-3-pyrazolidone, 1-phenyl-4,4-dimethyl-3-pyrazolidone, 1-phenyl-4-ethyl-3-pyrazolidone, 1-phenyl-5-methyl-3-pyrazolidone), or aminophenol derivative (e.g., o-aminophenol, p-aminophenol, N-methyl-o-aminophenol, N-methyl-p-aminophenol, 2,4-diaminophenol), or dihydroxybenzene derivative (e.g., hydroquinonemonosulfonate, sodium hydroquinonemonosulfonate, potassium 2,5-hydroquinonedisulfonate), is preferable. In case of the combined usage, the added amount of the developing agent consisting of 3-pyrazolidone derivative, aminophenol derivative or dihydroxybenzene is usually 0.01 to 0.2 moles per a liter of developer composition. Especially the combination of the ascorbic acid or its derivative with 3-pyrazolidone derivative, and the combination of the ascorbic acid or its derivative with 3-pyrazolidone derivative and dihydroxybenzene derivative is preferably used.

It is possible to add to a developer composition an alkali agent (sodium hydroxide and potassium hydroxide,), a pH buffer agent (e.g., carbonate, phosphate, borate, acetic acid, citric acid and Alkanol amine). As the pH buffer agent, carbonate is preferable, and an added amount of it is preferably 0.2 to 1.0 moles per a liter, more preferably 0.3 to 0.6 moles.

Sulfites as a preservative agent is preferably employed in case a compound represented by formula (A) is utilized. Preferable amount is 0.02–0.3 mol/l, more preferably 0.1–0.2 mol/l.

In case of need, a dissolving aid (e.g., polyethyleneglycol and its ester, Alkanol amine), a sensitizing agent (e.g., nonionic surfactant including polyoxyethylene and quaternary ammonium compound), a surfactant, anti-foaming agent and antifoggant (e.g., halogenide such as potassium bromide or sodium bromide, nitrobenzindazole, nitrobenzimidazole, benztriazole, benzthiazole, tetrazole and thiazole), a chelating agent (e.g., ethylenediaminetetraacetic acid or its alkali metal salt, nitrilotriacetate and polyphosphate), a development accelerating agent (e.g., compounds described in U.S. Pat. No. 2,304,025 and Japanese Patent Examined Publication No. 45541/1972), a hardening agent (e.g., glutaraldehyde or addition product of its metabisulfite), or an anti-foaming agent.

The pH of the developer composition is preferably adjusted to 7.5 to 10.4 with alkaline agents, more preferably 8.5 to 10.4. In case that pH is higher than 10.4, sufficient sensitivity and gradation of the invention are obtained, but fogging such as black spots increases a little, though they do not injure the advantage of the invention. On the other hand, in case that pH is lower than 7.5, sufficient effect of depressing fogging such as black spots, however, a little excess sensitivity and contrast are obtained though they do not injure the advantage of the invention.

As a fixing solution, any one which is popularly known in the art can be used. The pH of the fixing solution is usually between 3.0 and 8.0. As the fixing agent, for example, thiosulfates such as sodium thiosulfate, potassium thiosulfate, ammonium thiosulfate, and thiocyanates such as sodium thiocyanate, potassium thiocyanate, ammonium thiocyanate and other organic sulfur compounds which are capable of producing a stable silver complex salts and are known in the art as a fixing agent can be used.

Into the fixing solution, a compound which functions as a hardening agent, including, for example, water-soluble aluminum salts such as aluminum chloride, aluminum sulfate, potassium alum, aldehyde compounds (such as glutaraldehyde or its sulfite adduct, etc.) may be added.

The fixing solution may contain, if necessary, preservatives such as sulfites or metasulfites; pH buffers such as acetic acid, citric acid, etc.; pH adjuster such as sulfuric acid, or chelating agents capable of softening hard water, etc.

In the present invention concentration of the ammonium ion in the fixing composition is 0.1 mol or less per 1 l of the fixing composition.

The concentration of the ammonium ion in the fixing composition is preferably 0 to 0.05 mol/l. Sodium thiosulfate may be employed in place of ammonium thiosulfate as the fixing agent, or ammonium thiosulfate and sodium thiosulfate may be employed in combination.

In the present invention concentration of the acetic acid ion in the fixing composition is 0.33 mol or less per 1 l of the fixing composition. Source of the acetic acid can be selected optionally in the present invention as far as it dissociates acetic acid ion in the fixing composition. Preferable examples include acetic acid or it salt of lithium, potassium, sodium ammonium etc., and particularly preferable are sodium salt and ammonium salt. The concentration of the acetic acid ion in the fixing composition is 0.22 mol pr less, particularly less than 0.13 mol/l, whereby generation of acetic acid gas can be prevented remarkably. The most preferable embodiment is no acetic acid is contained.

The fixing agent contains a salt of citric acid, tartaric acid, malic acid, succinic acid or an optical isomer thereof. As the salt of these, lithium salt, potassium salt, sodium salt, and ammonium salt; hydrogen lithium salt, hydrogen potassium salt, hydrogen sodium salt, and hydrogen ammonium salt of tartaric acid; ammonium potassium salt of tartaric acid; and sodium potassium salt of tartaric acid can be mentioned. The preferable examples are citric acid, malic acid and tartaric acid, or their salt. The most preferable example is malic acid and its salt.

It is preferable to be subjected to water washing by water containing cleaning agent comprising an oxidizing agent or a bactericide in the present invention.

As an oxidizing agent used in the invention, are cited metallic or non-metallic oxide, oxygen acid or its salt, peroxide, and a compound including organic acid. From the viewpoint of discharging from draining pipe, as the aforesaid oxygen acid, sulfuric acid, nitrous acid, nitric acid and hypochlorous acid etc. are preferable, as the aforesaid peroxide, hydrogen peroxide and Fenton's reagent are especially preferable. The most preferable one is hydrogen peroxide.

The oxidizing agent is preferably supplied in a form of concentrated liquid or solid agent from the view point of distribution. Preferable is concentrated liquid which contains oxidizing component of 0.1 to 10 mol/l, particularly preferably 0.5 to 2.0 mol/l.

Concentrated liquid or solid oxidizing agent can be supplied by mixing with washing water in the present invention. They can be mixed before entering a wash tank, or may be mixed with washing water in the wash tank.

Replenishment timing accords with constant replenishment with every unit time or with every processed amount of the light-sensitive material by detecting the processed amount.

Adding amount of the oxidizing agent is preferably 0.5 to 10 mole equivalent to the amount of thiosulfate salt carried over by the light-sensitive material, more preferably 0.5 to 3 mole equivalent.

In this invention, the oxidizing agent is used in combination with preserving agent and bactericide so that the oxidizing agent functions more effectively.

As examples of the bactericides used in the invention which do not affect adverse effect on photographic characteristics, are cited thiazolylbenzimidazole derivative, isothiazolone derivative, chlorophenol derivative, bromophenol derivative, thiocyanic acid derivative, isothiocyanic acid derivative, acid azide derivative, diazine derivative, triazine derivative, thiourea derivative, alkylguanidine derivative, quaternary ammonium salt, organic tin compound, organic zinc compound, cyclohexylphenol derivative, imidazole derivative, benzimidazole derivative, sulfamide derivative, active halogen compound such as sodium chlorinated isocyanuric acid, chelate compound, sulfite compound, and antibiotics such as anti-bacteria and anti-mould represented by penicillin. Other bactericides described in "Water Quality Criteria" written by L. E. West in Phot. Sci. and Eng., vol 9, No. 6; various bactericides described in JP-A Nos. 57-8542, 58-105145, 59-126533, 55-111942 and 57-157244; compounds described in "Boukin boubai no Kagaku" (Chemistry of antibact and antifung.) written by Hiroshi Horiguchi, Sankyou Syuppan (1982), "Handbook of boukin boubai gijutu" (Technical handbook of antibact. and antifung.) edited by Japan antibact. and antifung. Society (Gihodo (1886), can be used.

The exemplified compounds are shown below.
1. 5-chloro-2-methyl-4-isothiazoline-3-one
2. 2-(4-thiazolyl)-benzimidazole
3. Methyl isothiocyanate
4. 3,5-dichloro-4'-fluoro-thiocarbanilide
5. 4-chloro-3,5-dimethylphenol
6. 2,4,6-trichlorophenol
7. Sodium dehydroacetic acid
8. Sulfanilamide
9. 3,4,5-tribromosalicylanilide
10. Potassium sorbate
11. Benzalkonium Chloride
12. 1-bromo-3-chloro-5,5-dimethylhydantoin
13. Monochloroacetamide
14. Monobromoacetamide
15. Monoiodoacetamide
16. Benzimidazole
17. Cyclohexylphenol
18. 2-octyl-isotiazoline-3-one
19. Ethylenediaminetetraacetic acid
20. Nitrilo-N,N,N-trimethinephosphonic acid
21. 1-hydroxyethane-1,1-diphosphonic acid
22. Ethlenediamine-N,N,N',N'-tetramethylenephosphonic acid
23. Sodium chlorinated isocyanurate
24. 2-methyl-4-isothiazoline-3-one
25. 10,10'-oxybisphenoxy arsine
26. 1,2-benzisothiazoline-3-one
27. Thiosalicylic acid The synthesizing methods and applied examples in other field of these exemplified compounds are described in U.S. Pat. Nos. 2,767,172, 2,767,173, 2,767,174, 2,870,015, U.K. Patent No. 848,130, France Patent No. 1,555,416. Some of them are in the market and trade names such as Predentol ON, Permachem PD, Topside 800, Topside EG5, Topside 300, Topside 600 (all of them are produced by Permachem Asia Co., Ltd.), Fineside J-700 (produced by Tokyo Finechemical Co., Ltd.), Prozel GXL (produced by I.C.I. Co., Ltd.) are available.

In cases where the above mentioned bactericides are supplied in washing water, adding amount is preferably 0.01 to 50 g/l, more preferably 0.05 to 20 g/l, and in cases where the above mentioned bactericides are supplied in cleaning composition, adding amount is preferably 0.1 to 50 g/l, more preferably 1 to 20 g/l.

Compounds having polyalkylene oxide chain represented by the following formula Po are preferable for a preserving agent employed in the present invention.

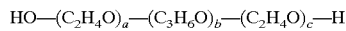

HO—$(C_2H_4O)_a$—$(C_3H_6O)_b$—$(C_2H_4O)_c$—H     Po:

A compound containing polyalkyleneoxide chain represented by the general formula Po used in the invention is the compound obtained from addition polymerization of propyleneglycol as a hydropobic group and ethyleneoxide. In this invention the compound having an average molecular weight of 2000 to 8500 is preferable, and content of molecular weight of polypropyleneglycol (PPG) in this compound is preferably 1400 to 2400. Weight present of ethyleneoxide in the total weight of the molecule is preferably 40 to 85%. Especially, in the formula, a+c is preferably about 150, b is preferably about 30. As the compound which meets these criteria, for example, non-ionic surfactant of trade name Pluronic Series, produced by Asahi Denka Co., Ltd. is usable, and exemplified surfactants listed below are preferable.

TABLE 1

| Compound No. | Trade name | Average molecular weight | PPG molecular weight | Ethyleneoxide in total molecule (Wt %) |
|---|---|---|---|---|
| 1 | Pluronic L44 | 2,200 | 1,200 | 40 |
| 2 | Pluronic L62 | 2,500 | 1,750 | 20 |
| 3 | Pluronic L64 | 2,900 | 1,750 | 40 |
| 4 | Pluronic L68 | 8,350 | 1,750 | 80 |
| 5 | Pluronic F68LF | 7,700 | 1,750 | 80 |

Adding amount of the compound containing polyakyleneoxide chain mentioned above is 1 to 1000 ppm to washing water, preferably 10 to 100 ppm, and in the case of using a purification agent, 0.01 to 10% to the oxidizing agent, preferably 0.1 to 5%.

As examples of the preserving agents used in the invention, are cited phosphoric acid, barbituric acid, urea, acetanilide, oxyquinoline, salicylic acid, quinolic acid, and their derivatives and their salts.

The cleaning agent employed in the invention preferably contains a chelating agent having chelate stability constant with calcium ion of 0.8 to 5.0. The chelate stability constant with calcium is logarithm of the formation constant when one calcium ion bonds to one of chelating agent, which is measured under the condition of temperature at 20° C. and ionic strength of 0.2. Examples of the cleaning agent are concretely organic acids such as maleic acid, gluconic acid, glucoheptanoic acid, tartaric acid, citric acid, succinic acid, salicylic acid, ascorbic acid, of erythorbic acid, glycin, amino polycarboxylic acids such as ethylenediamine tetraacetic acid, diethylenetriaminepentaacetic acid, of nitrilotriacetic acid, and those derivatives and their salts. Gluconic acid and citric acid are preferable among the organic acids, and, ethylenediamine tetraacetic acid, diethylenetriaminepentaacetic acid are preferable among aminopolycarboxylic acids. These compounds are employed in an amount of 0.005 to 0.2 mol, preferably 0.005–0.1 mol per wash water 1 l.

These compounds are employed in an amount of about 0.005 to 0.2 mol, preferably 0.005 to 0.1 mol per 1 l of washing water.

In case that the washing time is not more than 20 sec., the advantage of the invention is remarkable, and preferably 16 sec or less, particularly preferably 12 sec. or less.

In this invention, the solid processing composition of the fixing replenishment solution is the solid processing composition in the form of a tablet, a pellet or granules, and optionally treated with moisture proof. The solution in the form of paste or slurry is in semi-liquid form and inferior in storage stability. Any form of the solid processing composition which is accompanied with a danger in transferring it and is regulated to transfer it is not allowed to be used in this invention.

The powder is referred to an aggregate comprised of fine crystal particles. The granules are referred to granular material prepared by subjecting the powder to granulating process, having particle sizes of 50–5000 µm. The tablet is one prepared by subjecting the powder or granules to compression-molding to a given form.

Among the above mentioned solid processing compositions, the tablet is preferably used because it is accurate in replenishment and handled easily.

The processing composition can be solidified in any manner such that the processing composition in the form of a concentrated solution or fine powder or granules, is mixed with a water soluble binding agent and then the mixture is molded, or the water soluble binding agent is sprayed on the surface of temporarily-molded processing composition to form a covering layer. (Reference is made to JP Application Nos. 2-135887, 2-203165, 2-203166, 2-203167, 2-203168 and 2-300409.)

A preferred tablet-making process is to form a tablet by compression-molding after granulating powdery processing composition. Above mentioned tablet is improved in solubility and storage stability, resulting in the stability of photographic characteristics, compared with the solid processing composition formed by only mixing solid processing components and compression-molding components.

Granulation can be performed by the known method, such as rolling granulation, extrusion granulation, compression granulation, grinding granulation, stirring granulation, fluidized bed granulation and spray-drying granulation. It is preferred that the average grain size of the granules is 100 to 800 µm and preferably 200 to 750 µm. In particular, 60% or more of the granules is with a deviation of ±100 to 150 µm. As hydraulic press machine, any conventional compression molding machine, such as a single-engine compression molding machine, rotary-type compression machine, briquetting machine, etc. may be employed to form a tablet. Compression-molded (compression-tableted) solid processing composition may take any form and is preferably in a cylindrical form from the point of productivity, handling and problems of powder dust in cases when handled by user.

It is further preferred to granulate separately each component, such as an alkali agent, reducing agent and preservative in the above process.

The processing composition in the form of a tablet can be prepared according to methods, as described in JP-A Nos. 51-61837, 54-155038, 52-88025, and British Patent 1,213, 808. The granular processing composition can also be prepared according to methods, as described in JP-A Nos. 2-109042, 2-109043, 3-39735 and 3-39739. The powdery processing composition can be prepared according to methods, as described in JP-A No. 54-133332, British Patent 725,892 and 729,862 and German Patent 3,733,861.

In cases where the above mentioned solid processing composition is in the form of tablet, its bulk density is preferably 1.0 to 2.5 $g/cm^3$ from the viewpoint of solubility and the point of effects of the invention. When being not less than 1.0 $g/cm^3$, it is advantageous for strength of the solid composition; and when being not more than 2.5 $g/cm^3$, it is advantageous for solubility. In cases where the composition is in the form of granules or powder, the bulk density is preferably 0.40 to 0.95 $g/cm^3$.

The solid processing composition can be used for photographic processing composition such as developer composition, fixing composition and rinsing composition, but it is especially usable for developer composition from the viewpoint of stabilizing photographic characteristics.

Only a part of processing component in the solid processing composition used may be solidified. It is, however, preferable that the whole components of these processing chemicals are solidified. It is also preferable that the components thereof are each molded into a separate solid processing chemical and then individually packed in the same form. It is further preferable that the components are packed in series in the order of periodically and repeatedly adding them from the packages.

A preferable embodiment of a solid processing chemical applicable to the invention is that all of an alkali agent, a developing agent and a reducer are solidified when solidifying a developer, and that, when a developer is tableted, the numbers of the tablets may be not more than 4 tablets and, preferably, a single tablet. When the solid processing chemicals are solidified separately into not less than 2 tablets, it is preferable to pack these plural tablets or granules in the same package.

When a developer composition is solidified, it is preferable embodiment of the invention that an alkaline agent and reducing agent are all solidified in not more than three tablets, most preferably one or two tablets. When the composition is solidified in two or more composition, the plural tablets or granulated compositions are preferably packed in the same package.

The silver halide photosensitive material of the invention is processed by preferably an automatic processor. In this instance processing is made by replenishing certain amount of developer and fixer compositions proportional to the area of the photosensitive material. The replenishing amount of the developer and fixer compositions is not more than 300 ml per 1 m² to reduce waste liquid. Preferably 75 to 200 ml per 1 m².

The total processing time from the time of insertion of the front of film into an automatic processor to coming out of from the drying zone (dry to dry), is preferably 10 to 70 seconds for satisfying the demand for reducing the processing time. The total processing time includes all the time necessary for processing a black-and-white light-sensitive material, in concrete, includes the time necessary for all processing of, for example, the development, fixing, washing, stabilizing and drying, namely dry to dry. When the total processing time is less than 10 seconds, a satisfactory photographic property cannot be obtained since desensitization and lowering in contrast are occurred.

In the automatic processing machine drying zone employing heat conductive substance of 60° C. or higher (such as heat roller at 60 to 130° C.) or substances capable of emitting radiations with temperature higher than 150° C. (more preferably, higher than 250° C.), the following substances can be mentioned: tungsten, carbon, tantalum, Nichrome, a mixture of zirconium oxide, yttrium oxide and thorium oxide, carbon silicate, molybdenum disilicate. Further, methods of directly applying electricity to a radiating element such as tungsten, carbon, Nicrome, a mixture of zirconium oxide, yttrium oxide and thorium oxide to heat and emit radiation, or conducting thermal energy from a resistance pyrogeneous substance to a radiation emissive substance such as copper, stainless steel, nickel and various types of ceramics, to generate heat or radiate infrared rays may also be used to demonstrate the advantage of the present invention effectively.

The wasted developer composition can be regenerated by applying electric power. Concretely the regeneration is conducted by applying electric power to cathode (electric conductor or semiconductor such as stainless steal wool) in the developer waste and anode (insoluble electric conductor such as carbon, gold, platinum, titanium) in electrolyte liquid, wherein the waste developer tank and electrolyte tank are made contact through anion exchange membrane. The photosensitive material of the invention maybe processed while applying electric power. In this instance, various additives to the developer, for example, preservative, alkali agent, pH buffer, sensitizer, anti-foggant, silver-sludge preservative which may be added to the developer, may further be added.

EXAMPLES

The invention is described below referring examples.

Example 1

(Preparation of silver halide emulsion A-1)

A silver nitrate solution A, an aqueous solution B containing NaCl and KBr were added by double jet method to solution C for 7 min. while keeping silver potential (EAg) 120 mV, at pH 3.0, at the temperature of 35° C. whereby silver chlorobromide nucleus having grain size of 0.09 µm, composed of 70 mol % of silver chloride and 30 mol % of silver bromide. After that silver potential was adjusted to 100 mV with sodium chloride, aqueous silver nitrate solution D and aqueous water soluble halide E were added for 15 minutes, as a result, emulsion having grain size of 0.20 µm (variation coefficient 15%) composed of silver chloride 70 mol % and silver bromide 30 mol %. After that pH was adjusted to 5.6 with 1N NaOH aqueous solution, S-1 was added in an amount of $2 \times 10^{-4}$ mol per 1 mol of silver, and the emulsion was ripened for 10 minutes at 50° C. Then modified gelatin treated with phenylisocyanate was added and flock was washed at pH 4.2, 15 g of gelatin per 1 mol of silver was added after washing, pH was added to 5.7, and the emulsion was dispersed for 30 minutes at 55° C. After dispersion, $4 \times 10^{-4}$ mol of chloramine T per mol of silver was added. The pAg of thus obtained emulsion was 190 mV (40° C.).

| | | |
|---|---|---|
| A: | Silver nitrate | 16 g |
| | Nitric acid (5%) | 5.3 ml |
| | Ion-exchanged water | 48 ml |
| B: | NaCl | 3.8 g |
| | KBr | 3.5 g |
| | Ossein gelatin | 1.7 g |
| | Ion-exchanged water | 48 ml |
| C: | NaCl | 1.4 g |
| | Ossein gelatin | 7 g |
| | Nitric acid (5%) | 6.5 ml |
| | $K_2RhCl_5$ ($H_2O$) | 0.06 mg |
| | Ion-exchanged water | 700 ml |
| D: | Silver nitrate | 154 g |
| | Nitric acid (5%) | 4.5 ml |
| | Ion-exchanged water | 200 ml |
| E: | NaCl | 37 g |
| | KBr | 33 g |
| | Ossein gelatin | 6 g |
| | $K_2RhCl_5$ ($H_2O$) | 0.04 mg |
| | Ion-exchanged water | 200 ml |

To the emulsion were added $1.5 \times 10^{-3}$ mol per mol of silver of 4-hydroxy-6-methyl-1,3,3a,7-tetrazaindene and $8.5 \times 10^{-4}$ mol per mol of silver of potassium bromide, and adjusted to be pH 5.6 and EAg 123 mV.

To the resulting emulsion were added flower of sulfur ($2 \times 10^{-5}$ mol of sulfur atom per mol of silver) in a fine particle dispersion and $1.5 \times 10^{-5}$ mol of chloroauric acid per mol of silver and the resulting emulsion was chemically ripened at 60° C. for 80 min. After the ripening, $2 \times 10^{-3}$ mol per mol of silver of 4-hydroxy-6-methyl-1,3,3a,7-tetrazaindene, $3 \times 10^{-4}$ mol per mol of silver of 1-phenyl-5-mercaptotetrazole and $1.5 \times 10^{-3}$ mol per mol of silver of potassium iodide were added. After the emulsion was cooled to 40° C., to this emulsion was added sensitizing dyes S-1 in an amount of $2 \times 10^{-4}$ mol per mol of silver.

(Preparation of silver halide emulsion A-2)

Silver bromochloride nucleus was prepared in the same way except that the amount of $K_2RhCl_5(H_2O)$ was changed to 0.1 mg and the temperature of mixing was changed to 40° C., resulting nucleus composed of 70 mol % of silver chloride and 30 mol % of silver bromide, and having grain size of 0.25 µm (variation coefficient 15%).

Thereafter chemical ripening and spectral sensitization were given in the same way as emulsion A-1.
Preparation of sample 101

Solid dye dispersion layer, silver halide emulsion layer and emulsion protective layer having composition as shown below, were simultaneously coated on a subbed support. After the layers being cooled and set, on a subbed support opposite to the emulsion layer, backing layer and backing protective layer were coated simultaneously and were cooled and set at −1° C., and then both side were simultaneously dried. Thus samples No. 101 was obtained.

| Preparation of coating composition | |
|---|---|
| Solid dye dispersion layer | |
| Gelatin | 1.0 g/m² |
| Solid dispersion dye AD-8 | 15 mg/m² |
| Water soluble dye F-1 | 5 mg/m² |
| Polymer latex L-2 (particle size of 0.2 μm) | 0.3 g/m² |
| Sodium dodecylbenzenesulfonate | 20 mg/m² |
| Silver halide emulsion layer | |
| Silver halide emulsion A-1 (Ag amount) | 3.3 g/m² |
| Gelatin | 1.5 g/m² |
| Comparative hydrazine 1 | 30 mg/m² |
| Polymer latex L-1 (Particle size 0.10 μm) | 0.5 g/m² |
| Suspension polymerization product of colloidal silica 75 wt %, vinyl acetate 12.5 wt % and vinylpyvalinate 12.5 wt % | 1.0 g/m² |
| Saponin | 20 mg/m² |
| 2-Mercapto-6-hydroxypurine | 2 mg/m² |
| Ascorbic acid | 20 mg/m² |
| EDTA 2Na | 25 mg/m² |
| Sodium polystyrene sulfonate (Average molecular weight 500,000) | 15 mg/m² |
| pH 5.2 | |
| Intermediate layer | |
| Gelatin | 0.32 g/m² |
| Nucleation accelerator (Amine compound Na-3) | 12.9 mg/m² |
| Polymer latex (particle size: 0.10 μm) | 0.3 g/m² |

-continued

| Preparation of coating composition | |
|---|---|
| Sodium polystyrenesulfonate (average m.w.:500,000) | 10 mg/m² |
| Protective layer | |
| Gelatin | 0.48 g/m² |
| Water soluble dye F-2 | 50 mg/m² |
| Sodium isoamyl-n-dodecylsulfosuccinate | 12 mg/m² |
| SXA-1 | 0.6 mg/m² |
| Matting agent (amorphous silica, average particle size:3 μm) | 22.5 mg/m² |
| Propyl gallate | 90 mg/m² |
| Dimethyl siloxane (average m.w. 100,000) dispersion (average particle size:0.2 μm) | 12 mg/m² |
| Hardening agent (1) | 30 mg/m² |
| Sodium polystyrene sulfonate | 10 mg/m² |
| Bactericide Z | 0.5 mg/m² |
| Backing layer | |
| Gelatin | 3.0 g/m² |
| Sodium isoamyl-n-dodecylsulfosuccinate | 5 mg/m² |
| Compound D | 50 mg/m² |
| Polymer latex L-3 | 0.3 g/m² |
| Colloidal silica (average particle size 0.05 μm) | 50 mg/m² |
| Sodium polystyrene sulfonate | 10 mg/m² |
| Dye F-3 | 120 mg/m² |
| Dye F-4 | 15 mg/m |
| Dye F-5 | 37 mg/m² |
| 1-phenyl-5-mercaptotetrazole | 3 mg/² |
| Hardening agent (1) | 100 mg/m² |
| Backing protective layer | |
| Gelatin | 1.1 g/m² |
| Mating agent (mono dispersed polymethylmethacrylate, average particle size 3 μm) | 45 mg/m² |
| Sodium di-(2-ethylhexyl) sulfosuccinate | 10 mg/m² |

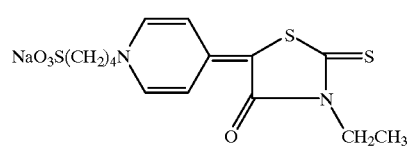

S-1

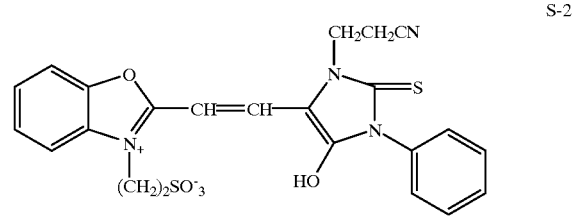

S-2

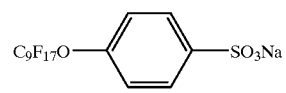

SA-1

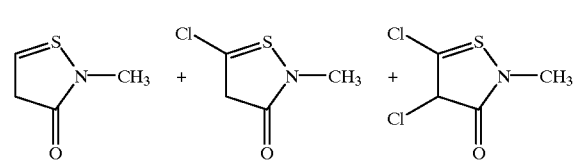

z

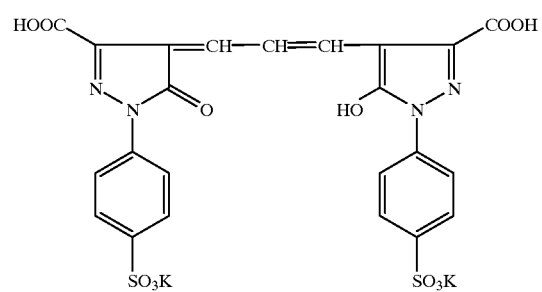

F-1

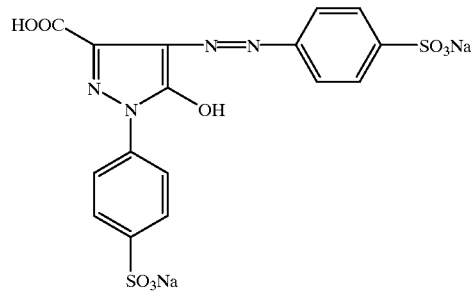

F-2

-continued

F-3

[Structure F-3: bis-pyrazolone methine dye with two N-phenyl-SO₃K groups]

F-4

[Structure F-4: pyrazolone with HOOC, linked via –CH=CH–CH= to p-N(CH₃)₂-phenyl; N-phenyl-SO₃K]

F-5

[Structure F-5: triarylmethine cation with two p-N(CH₃)₂ groups and a phenyl bearing CH₂SO₃⁻ and CH₂SO₃H]

L-1

$$\left(-CH_2-\underset{\underset{COO-\text{cyclohexyl}}{|}}{\overset{\overset{CH_3}{|}}{C}}-\right)_{60}\left(-CH_2-\underset{COOC_9H_{19}}{CH}-\right)_{30}\left(-CH_2-\underset{COOCH_2-CH-CH_2}{\underset{O}{CH}}-\right)_{10}$$

L-2

$$-(CH_2-CH)_{60}-(CH_2-\underset{COOC_4H_9}{CH})_{38.5}-(CH_2-\underset{COOH}{CH})_{1.5}-$$
(with phenyl on first unit)

L-3

$$\left(-CH_2-\underset{\underset{Cl}{|}}{\overset{\overset{Cl}{|}}{C}}-\right)_{50}\left(-CH_2-\underset{COOC_4H_9}{CH}-\right)_{50}$$

Hardner (1)

$(CH_2\!=\!CH\!-\!SO_2CH_2CONHCH_2)_2\!-$

D $C_9H_{19}\!-\!\!\!\bigcirc\!\!\!-O(CH_2CH_2O)_{35}H$

Samples 102 to 135 were prepared in the same way as sample 101 except that the hydrazine compound was replaced shown in Table 2.

Estimation of Samples

Samples were estimated in the following way, and the result is shown in Table 2.

Sensitivity and Contrast

Samples were subjected to wedgewise exposure employing 660 nm semiconductor laser, and were processed by an automatic developing machine LD-T1100 (manufactured by Dainippon Screen Mfg., Co.) with the processing composition and the processing condition described below.

Processed samples were subjected to sensitometry using densitometer PDA-65 (Konica Digital Densitometer). Sensitivity was shown as a relative value at a density of 1.0, based on the sensitivity of Sample 101 being 100. The contrast γ was obtained by the following formula taking E(0.05) as reciprocal value of exposure amount to give density of 0.05 and E(2.5) as reciprocal value of exposure amount to give density of 2.5.

$\gamma=2.45/(E(0.05)-E(2.5))$

Pepper fog

Processed samples each were also visually observed by 40 times magnifier and the number of pepper fog were counted in 2 mm×2 mm area of the visual field. Processing condition

| | Temperature | Time |
|---|---|---|
| Developing | 35° C. | 30 sec. |
| Fixing | 35° C. | 20 sec. |
| Washing | room | 20 sec. |
| Drying | 45° C. | 30 sec. |
| Total | | 100 sec. |

Composition of processor

Developer A, per 1l working liquid

| | |
|---|---|
| Pentasodium diethylenetriaminepentaacetate | 4 g |
| Sodium sulfite | 55 g |

-continued

| | |
|---|---|
| Potassium carbonate | 10 g |
| Potassium carbonate | 60 g |
| Hydroquinone | 22 g |
| 1-phenyl-5-methyl4'-hydroxymethyl-3-pyrazolidone | 1.5 g |
| Sodium erythorbate | 2 g |
| 1-phenyl-5-mercaptotetrazole | 0.03 g |
| Potassium bromide | 4 g |
| benzotriazole | 0.25 g |
| Diethyleneglycol | 40 g |
| 8-mercaptoadenine | 0.12 g |
| KOH to make pH 10.4 | |
| (Developer B) | |
| Diethyienetriaminepentaacetate | 1 g |
| Sodium sulfite | 40 g |
| Potassium carbonate | 40 g |
| Potassium hydrogencarbonate | 16 g |
| 1-Phenyl-4-methyl,4'-hydroxymethyl-3-Pyrazolidone | 1.5 g |
| Sodium erythorbate monohydrate | 55 g |
| 1-Phenyl-5-mercaptotetrazole | 0.03 g |

-continued

| | |
|---|---|
| Potassium bromide | 4 g |
| Benzotriazole | 0.25 g |
| Diethyleneglycol | 40 g |
| 8-Mercaptoadenine | 0.06 g |
| KOH to make pH 9.8 | |
| (Fixer Composition, per 1 liter of working liquid) | |
| Deionized water | 216 ml |
| Sodium thiosulfate | 140 g |
| Sodium sulfite | 22 g |
| Boric acid | 10 g |
| Tartaric acid | 3 g |
| Sodium acetate 3 hydrate | 37.8 g |
| Acetic acid (90 % aqueous solution) | 13.5 g |
| Aluminum sulfate 18 hydrate | 18 g |

According to above described recipe the composition was dissolved and water was added to make up 400 ml. The concentrated liquid described above is mixed with deionized water 600 ml as employed. Working liquid has pH of 4.83.

TABLE 2

| No. | Hydrazine compound Kind | *1 | Amount mg/m$^2$ | Developer | Sensitivity | γ | Pepper spots |
|---|---|---|---|---|---|---|---|
| 101 | Comparative 1 | 0 | 30 | A | 100 | 8 | 20 |
| 102 | Comparative 2 | 0 | 30 | A | 105 | 11 | 15 |
| 103 | Comparative 3 | 4 | 30 | A | 110 | 13 | 7 |
| 104 | Comparative 4 | 3 | 30 | A | 108 | 13 | 6 |
| 105 | Comparative 5 | 3 | 30 | A | 109 | 15 | 5 |
| 106 | Comparative 1 | 0 | 30 | B | 80 | 6 | 30 |
| 107 | Comparative 2 | 0 | 30 | B | 85 | 8 | 20 |
| 108 | Comparative 3 | 4 | 30 | B | 90 | 9 | 15 |
| 109 | Comparative 4 | 3 | 30 | B | 92 | 10 | 8 |
| 110 | Comparative 5 | 3 | 30 | B | 93 | 12 | 10 |
| 111 | H1-1 | 3 | 20 | A | 125 | 28 | 5 |
| 112 | H1-6 | 6 | 20 | A | 116 | 23 | 3 |
| 113 | H1-7 | 3 | 20 | A | 130 | 30 | 1 |
| 114 | H1-10 | 3 | 20 | A | 125 | 25 | 2 |
| 115 | H1-19 | 6 | 20 | A | 115 | 21 | 4 |
| 116 | H1-1 | 3 | 20 | B | 120 | 25 | 4 |
| 117 | H1-6 | 6 | 20 | B | 115 | 23 | 3 |
| 118 | H1-7 | 3 | 20 | B | 133 | 33 | 1 |
| 119 | H1-10 | 3 | 20 | B | 127 | 28 | 2 |
| 120 | H1-19 | 6 | 20 | B | 116 | 20 | 3 |
| 121 | H1-32 | 3 | 20 | B | 125 | 21 | 2 |
| 122 | H1-1/H2-1 | 3/– | 20/15 | A | 125 | 25 | 2 |
| 123 | H1-3/H2-6 | 3/– | 20/15 | A | 125 | 28 | 2 |
| 124 | H1-7/H2-14 | 3/– | 20/15 | A | 130 | 28 | 2 |
| 125 | H1-7/H2-15 | 3/– | 20/15 | A | 135 | 35 | 1 |
| 126 | H1-7/H2-20 | 3/– | 20/15 | A | 131 | 26 | 2 |
| 127 | H1-7/H2-25 | 3/– | 20/15 | A | 128 | 25 | 2 |
| 128 | H1-19/H2-15 | 6/– | 20/15 | A | 122 | 23 | 3 |
| 129 | H1-1/H2-1 | 3/– | 20/15 | B | 125 | 26 | 1 |
| 130 | H1-3/H2-6 | 3/– | 20/15 | B | 126 | 28 | 1 |
| 131 | H1-7/H2-14 | 3/– | 20/15 | B | 130 | 30 | 1 |
| 132 | H1-7/H2-15 | 3/– | 20/15 | B | 137 | 37 | 0 |
| 133 | H1-7/H2-20 | 3/– | 20/15 | B | 130 | 31 | 1 |
| 134 | H1-7/H2-25 | 3/– | 20/15 | B | 126 | 25 | 2 |
| 135 | H1-19/H2-15 | 6/– | 20/15 | B | 121 | 23 | 3 |
| 136 | H1-33 | 3 | 20 | A | 112 | 18 | 5 |
| 137 | H1-33 | 3 | 20 | B | 113 | 19 | 5 |
| 138 | H1-34/H2-20 | 3/–1 | 20/15 | A | 118 | 20 | 4 |
| 139 | H1-34/H2-20 | 3/–1 | 20/15 | B | 119 | 21 | 4 |

*1: Number of branches in alkyl group

TABLE 2-continued

| | Hydrazine compound | | Amount | | | | |
|---|---|---|---|---|---|---|---|
| No. | Kind | *1 | mg/m² | Developer | Sensitivity | γ | Pepper spots |

Comparative Hydrazine 1

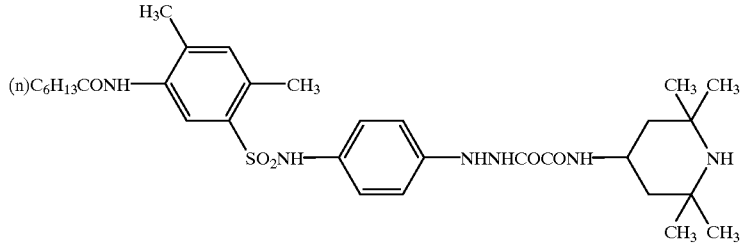

Comparative Hydrazine 2

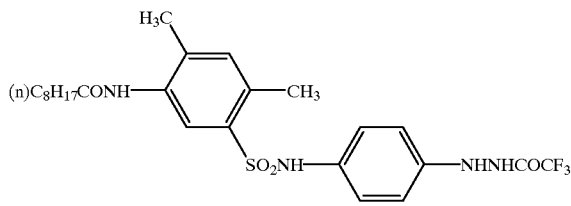

Comparative Hydrazine 3

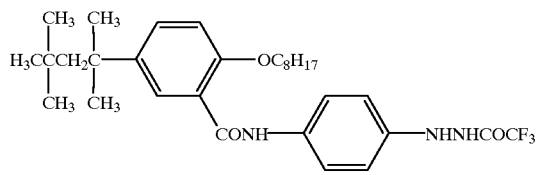

Comparative Hydrazine 4

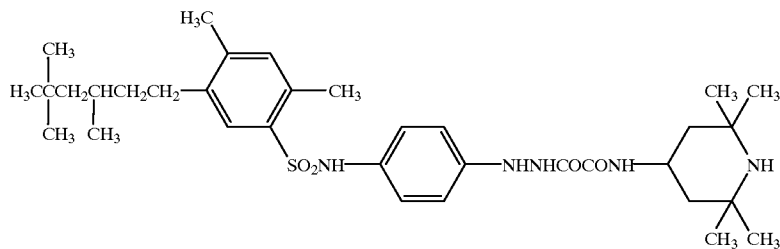

Comparative Hydrazine 5

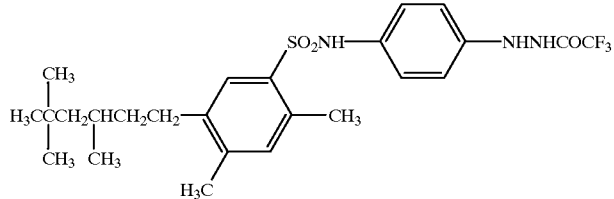

Comparative samples show lower sensitivity and γ, and more pepper spots as apparent from the table 2. Further extreme reduction of sensitivity and γ and occurrence of many pepper spots are found when the developer B is employed in comparison with developer A. Contrary the samples of the invention show high sensitivity and γ as well as little pepper spots.

The case of having two or less branches is outside of the invention, which is not preferable because of reduced sensitivity and γ in comparison with the hydrazine compound of the invention. And fog called pepper spots tends to occur. The case of having three or more branches is the invention, and it is found preferably 3 to 6, particularly 3.

What is claimed is:

1. A silver halide photographic photosensitive material having a light sensitive silver halide emulsion layer provided on a support wherein the silver halide photographic photosensitive material comprising a hydrazine compound having at least one alkyl group which has no atom other than carbon and hydrogen atoms, has three or more branches, and does not bond to aromatic ring directly.

2. The silver halide photographic photosensitive material of claim 1 wherein total number of carbon atoms of the alkyl group in the hydrazine compound is 6 to 10.

3. The silver halide photographic photosensitive material of claim 2 wherein the alkyl group is 2,4,4-trimethylpentyl group.

4. The silver halide photographic photosensitive material of claim 1 wherein the hydrazine compound is represented by formula (1), Formula (1)

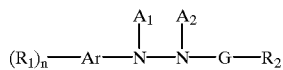

wherein $R_1$ is a group containing an alkyl group which has no atom other than carbon, has three or more branches, and does not bond to aromatic ring directly; n is an integer of 0 to 3; Ar is an aromatic group, $A_1$ and $A_2$ are both are hydrogen atom or one of them is a hydrogen atom and the other is an alkylsulfonyl or acyl group; $R_2$ represents alkyl group, aryl group, heteroaryl group, alkenyl group, alkoxy group or amino group; and G is —(CO)p— group, sulfonyl group, sulfoxy group, —P(=O)$R_3$— group or iminomethylene group, p is an integer of 1 or 2, $R_3$ is alkyl group, alkenyl group, alkynyl group, aryl, alkoxy group, alkenyloxy group, alkynyloxy group, aryloxy group or amino group.

5. The silver halide photographic photosensitive material of claim 4 wherein total number of carbon atoms of the alkyl group contained in a group represented by $R_1$ in the formula (1) is 6 to 10.

6. The silver halide photographic photosensitive material of claim 5 wherein the alkyl group contained in a group represented by $R_1$ is 2,4,4-trimethylpentyl group.

7. The silver halide photographic photosensitive material of claim 4 wherein $R_1$ is acylamino group, carbamoyl group, ureide group, amino group, sulfonyl amino group or alkylthio group each of which contains an alkyl group having three or more branches but no atom other than carbon.

8. The silver halide photographic photosensitive material of claim 7 wherein $R_1$ is acylamino group which contains an alkyl group having three or more branches but no atom other than carbon.

9. The silver halide photographic photosensitive material of claim 4 wherein $R_2$ of a formula (1) is trifluoromethyl group.

10. The silver halide photographic photosensitive material of claim 1 wherein the hydrazine compound is represented by formula (2), Formula (2)

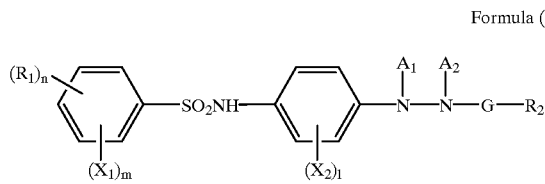

wherein $R_1$ is a group containing an alkyl group which has no atom other than carbon and hydrogen atoms, has three or more branches, and does not bond to aromatic ring directly; n is an integer of 0 to 3; $A_1$ and $A_2$ are both are hydrogen atom or one of them is a hydrogen atom and the other is an alkylsulfonyl or acyl group; $R_2$ represents alkyl group, aryl group, heteroaryl group, alkenyl group, alkoxy group or amino group; and G is —(CO)p— group, sulfonyl group, sulfoxy group, —P(=O)$R_3$— group or iminomethylene group, p is an integer of 1 or 2, $R_3$ is alkyl group, alkenyl group, alkynyl group, aryl, alkoxy group, alkenyloxy group, alkynyloxy group, aryloxy group or amino group; $X_1$ and $X_2$ represent a hydrogen atom or a group which can be substituted for benzene ring; m and l each represents an integer of 0 to 4, with proviso m+n<5.

11. The silver halide photographic photosensitive material of claim 9 wherein number of carbon atoms of the alkyl group contained in a group represented by $R_1$ in the formula (2) is 6 to 10.

12. The silver halide photographic photosensitive material of claim 9 wherein $R_1$ is acylamino group, carbamoyl group, ureide group, amino group, sulfonyl amino group or alkylthio group each of which contains an alkyl group having three or more branches but no atom other than carbon.

13. The silver halide photographic photosensitive material of claim 9 wherein $R_1$ is acylamino group which contains an alkyl group having three or more branches but no atom other than carbon.

14. The silver halide photographic photosensitive material of claim 9 wherein the alkyl group contained in a group represented by $R_1$ in the formula (2) is 2,4,4-trimethylpentyl group.

15. The silver halide photographic photosensitive material of claim 9 wherein the alkyl group contained in a group represented by $R_2$ in the formula (2) is trifluoromethyl group.

16. The silver halide photographic photosensitive material of claim 1 wherein the silver halide photographic photosensitive material further comprises a hydrazine compound the following formula (3), Formula (3)

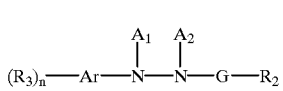

wherein the formula $R_3$ represents a group containing at least one two valent sulfur atom; n is an integer of 0 to 3; Ar is an aromatic group, $A_1$ and $A_2$ are both are hydrogen atom or one of them is a hydrogen atom and the other is an alkylsulfonyl or acyl group; $R_2$ represents alkyl group, aryl group, heteroaryl group, alkenyl group, alkoxy group or amino group; and G is —(CO)p— group, sulfonyl group, sulfoxy group, —P(=O)$R_3$— group or iminomethylene group, p is an integer of 1 or 2, $R_3$ is alkyl group, alkenyl group, alkynyl group, aryl, alkoxy group, alkenyloxy group, alkynyloxy group, aryloxy group or amino group.

17. The silver halide photographic photosensitive material of claim 16 wherein $R_3$ in the formula (3) is a group containing alkylthio group having 8 or less carbon atoms.

18. The silver halide photographic photosensitive material of claim 16 wherein $R_3$ in the formula (3) is trifluoromethyl group.

19. A silver halide photographic photosensitive material having a light-sensitive silver halide emulsion layer provided on a support wherein the silver halide photographic photosensitive material comprises a hydrazine compound having at least one alkyl group selected from the group consisting of (R-1) 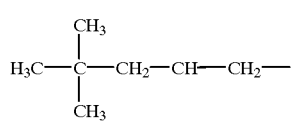
(R-2) 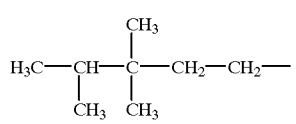
(R-3) 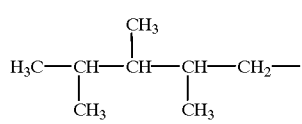
(R-4) 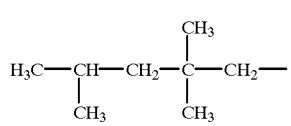
(R-5) 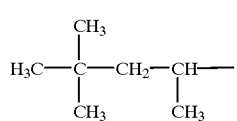
(R-6) 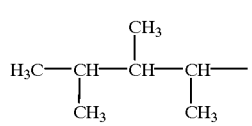
(R-7) 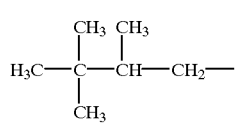
(R-8) 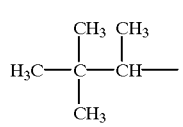
(R-9) 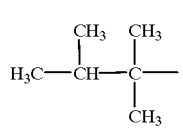
(R-10) 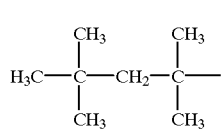
-continued
(R-11) 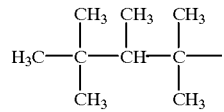
(R-12) 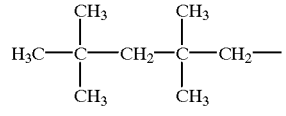
(R-13) 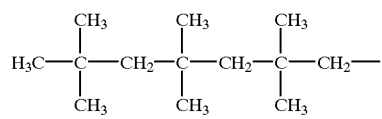
(R-14) 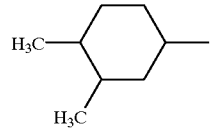
(R-15) 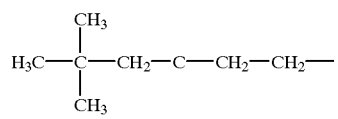
(R-16) 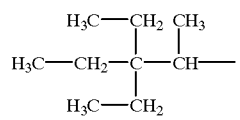
(R-17) (R-18) 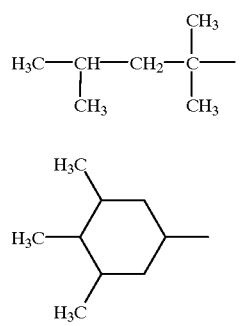
(R-19) 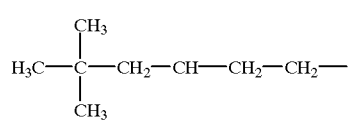
(R-20) 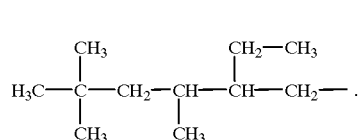
20. A silver halide photographic photosensitive material having a light-sensitive silver halide emulsion layer provided on a support wherein the silver halide photographic photosensitive material comprises a hydrazine compound selected from the group consisting of

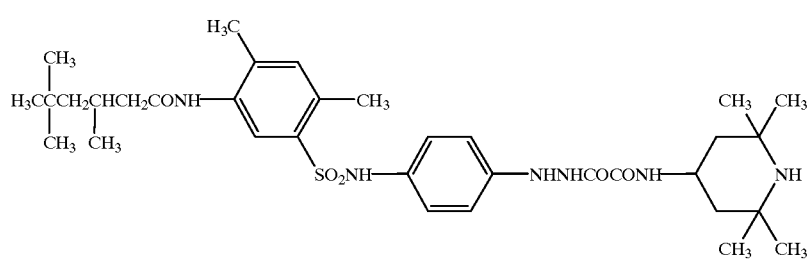
H1-1
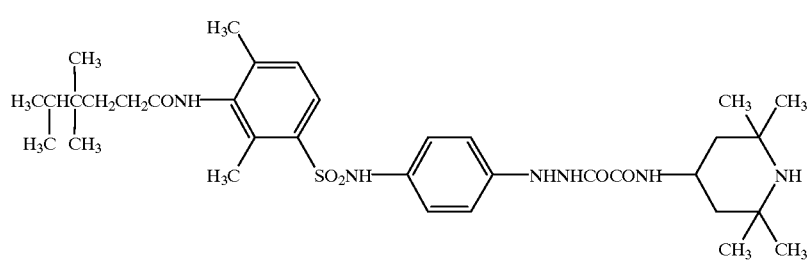
H1-2
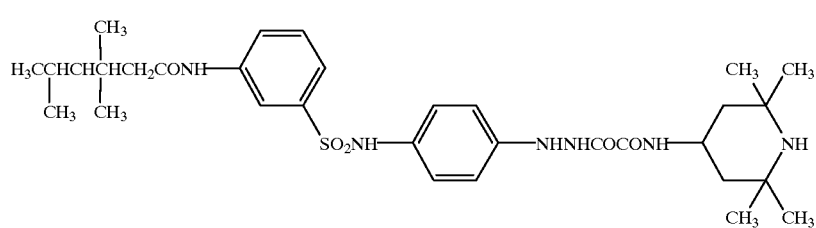
H1-3
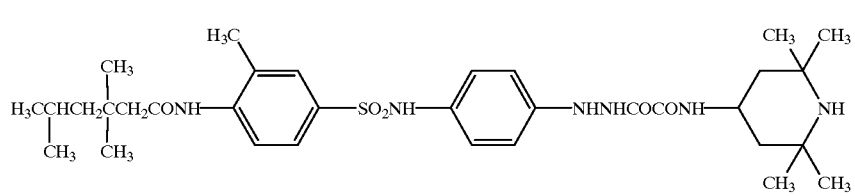
H1-4
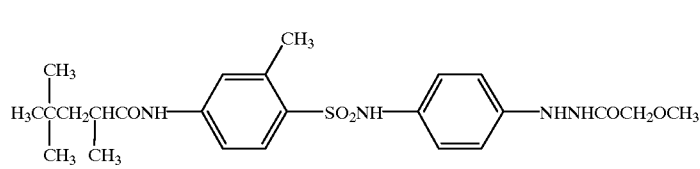
H1-5
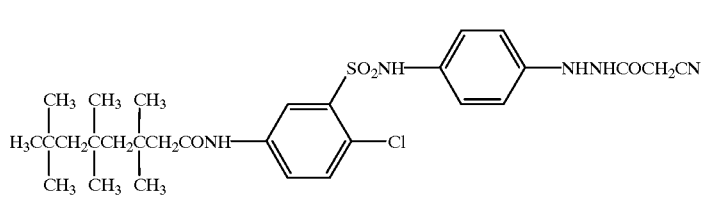
H1-6
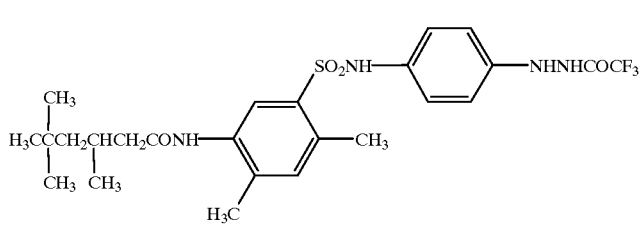
H1-7

-continued
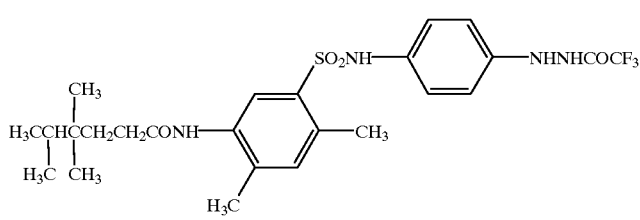 H1-8
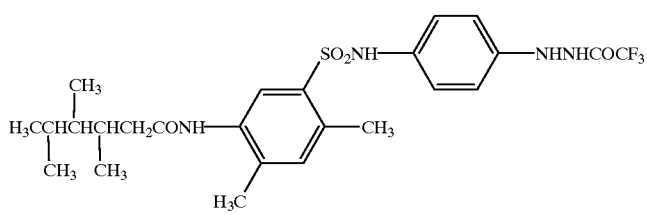 H1-9
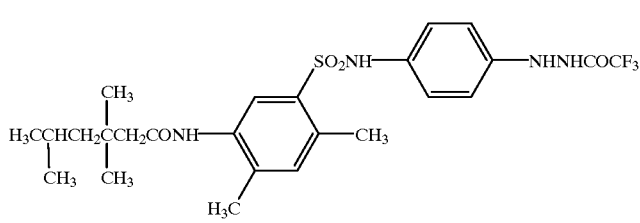 H1-10
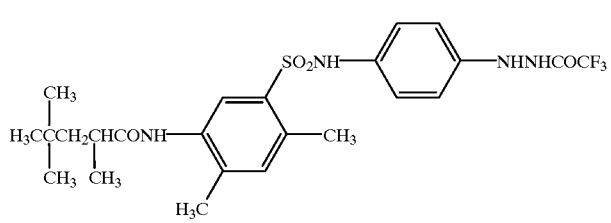 H1-11
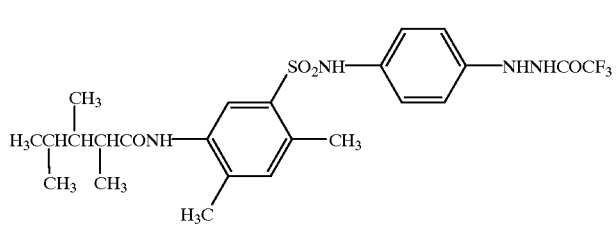 H1-12
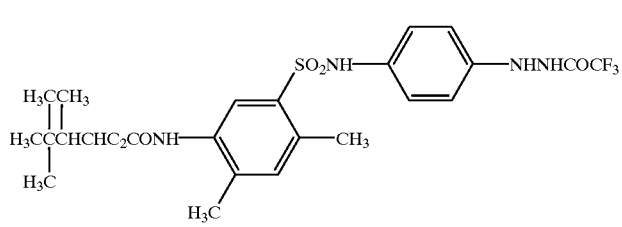 H1-13
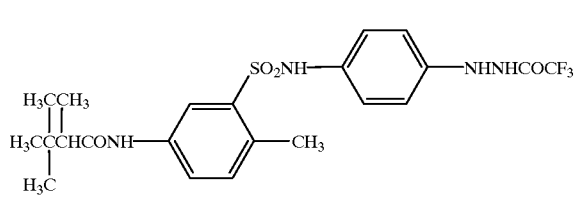 H1-14

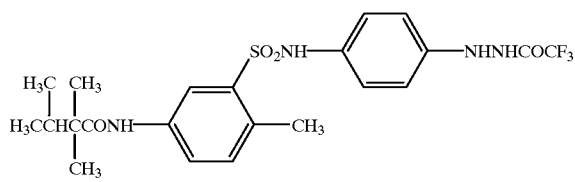
H1-15
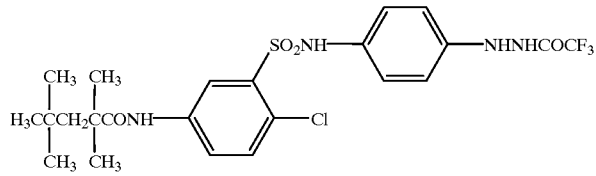
H1-16
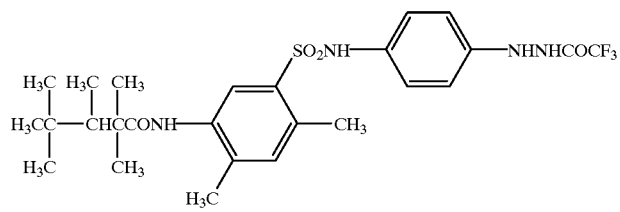
H1-17
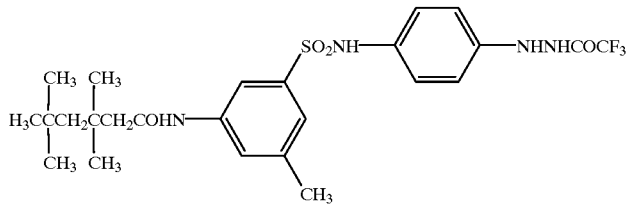
H1-18
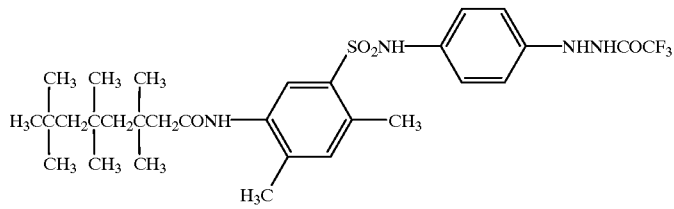
H1-19
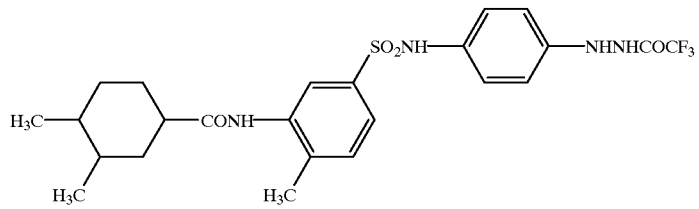
H1-20
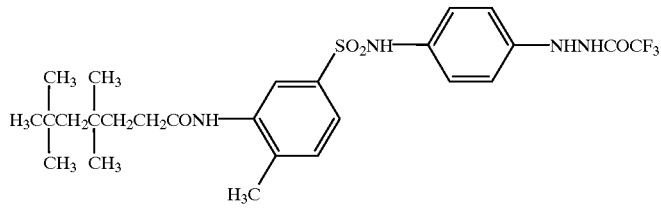
H1-21

-continued
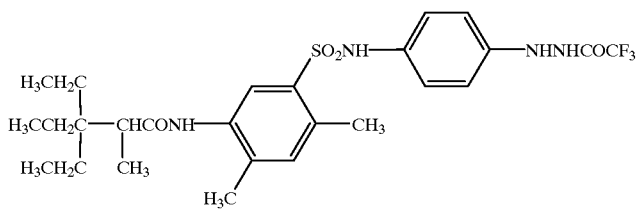
H1-22
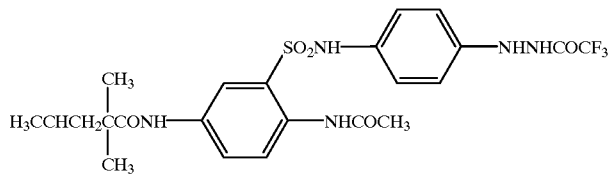
H1-23
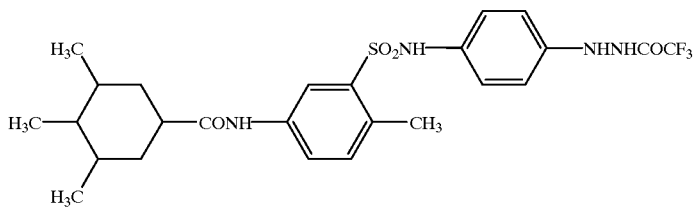
H1-24
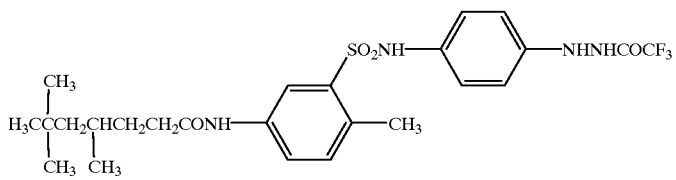
H1-25
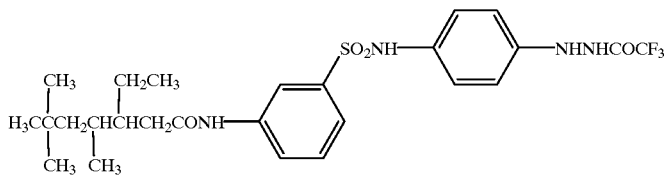
H1-26
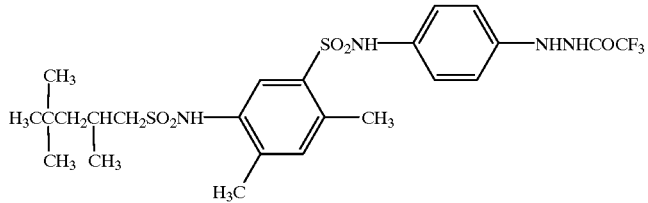
H1-27
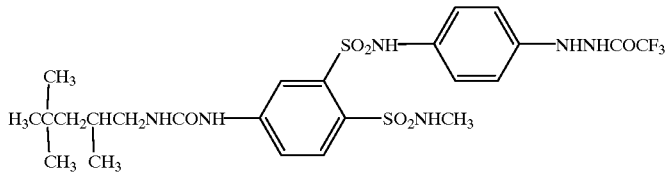
H1-28

-continued
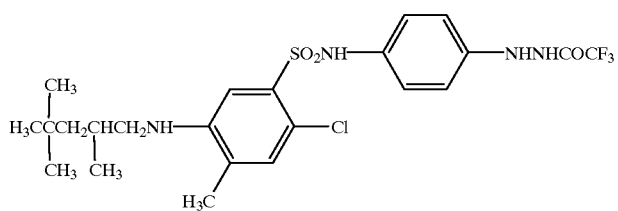
H1-29
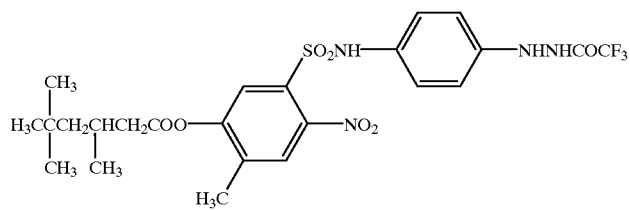
H1-30
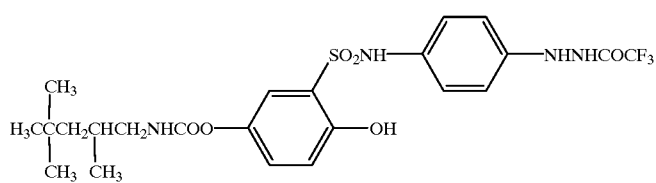
H1-31
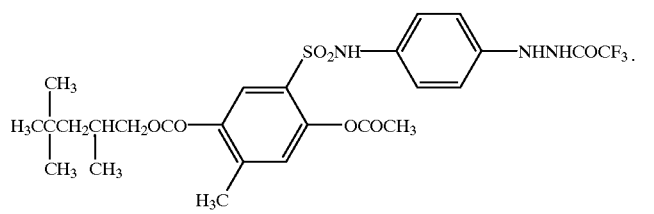
H1-32
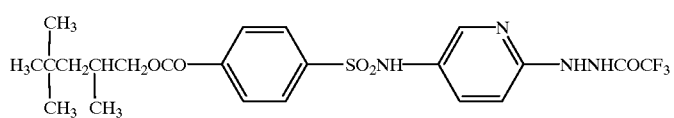
H1-33
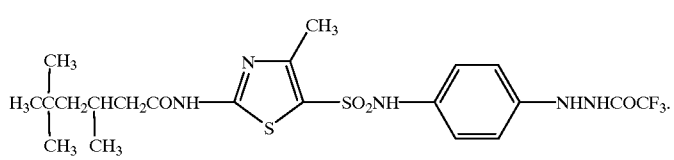
H1-34
\* \* \* \* \*